United States Patent
Gonzalez-Hernandez

(10) Patent No.: US 9,271,772 B2
(45) Date of Patent: Mar. 1, 2016

(54) SYSTEM AND METHOD FOR FRACTURE REPLACEMENT OF COMMINUTED BONE FRACTURES OR PORTIONS THEREOF ADJACENT BONE JOINTS

(71) Applicant: Eduardo Gonzalez-Hernandez, Miami, FL (US)

(72) Inventor: Eduardo Gonzalez-Hernandez, Miami, FL (US)

(73) Assignee: TOBY ORTHOPAEDICS, INC., Coral Cables, FL (US)

( * ) Notice: Subject to any disclaimer, the term of this patent is extended or adjusted under 35 U.S.C. 154(b) by 117 days.

(21) Appl. No.: 13/663,209

(22) Filed: Oct. 29, 2012

(65) Prior Publication Data

US 2014/0121709 A1    May 1, 2014

Related U.S. Application Data

(60) Provisional application No. 61/552,387, filed on Oct. 27, 2011.

(51) Int. Cl.
| | | |
|---|---|---|
| A61F 2/40 | (2006.01) |
| A61B 17/80 | (2006.01) |
| A61F 2/42 | (2006.01) |
| A61B 17/86 | (2006.01) |

(Continued)

(52) U.S. Cl.
CPC ........... *A61B 17/8061* (2013.01); *A61F 2/4003* (2013.01); *A61F 2/4261* (2013.01); *A61B 17/746* (2013.01); *A61B 17/809* (2013.01); *A61B 17/8635* (2013.01); *A61F 2/30739* (2013.01); *A61F 2002/3052* (2013.01); *A61F 2002/3092* (2013.01); *A61F 2002/30332* (2013.01); *A61F 2002/30352* (2013.01); *A61F 2002/30387* (2013.01); *A61F 2002/30433* (2013.01); *A61F 2002/4007* (2013.01); *A61F 2002/4025* (2013.01); *A61F 2002/4066* (2013.01); *A61F 2002/4264* (2013.01); *A61F 2002/4266* (2013.01); *A61F 2002/4269* (2013.01)

(58) Field of Classification Search
CPC ..... A61F 2/3601; A61F 2/4637; A61B 17/68; A61B 17/74
See application file for complete search history.

(56) References Cited

U.S. PATENT DOCUMENTS

| | | | |
|---|---|---|---|
| 1,950,799 A | 3/1934 | Jones |
| 2,500,370 A | 3/1950 | McKibbin |
| 2,555,291 A | 5/1951 | Poupitch |

(Continued)

FOREIGN PATENT DOCUMENTS

| | | | |
|---|---|---|---|
| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.

(Continued)

*Primary Examiner* — Sameh Boles
(74) *Attorney, Agent, or Firm* — Martin & Ferraro, LLP

(57) ABSTRACT

A system and method facilitating replacement of comminuted bone fractures or portions thereof adjacent bone joints. The system and method employs a prosthesis to replace at least a portion of the comminuted bone fractures. The prosthesis serves in reproducing the articular surface of the portion or portions of the comminuted bone fractures that are replaced. In doing so, the prosthesis serves in restoring joint viability and corresponding articulation thereof.

9 Claims, 9 Drawing Sheets

(51) Int. Cl.
*A61F 2/30* (2006.01)
*A61B 17/74* (2006.01)

(56) References Cited

U.S. PATENT DOCUMENTS

| | | | |
|---|---|---|---|
| 2,682,265 A | 6/1954 | Collison |
| 2,875,663 A | 3/1959 | Weiber |
| 3,489,143 A | 1/1970 | Halloran |
| 3,552,389 A | 1/1971 | Allgower et al. |
| 3,579,831 A | 5/1971 | Stevens et al. |
| 3,716,050 A | 2/1973 | Johnston |
| 3,791,380 A | 2/1974 | Dawidowski |
| 3,900,025 A | 8/1975 | Barnes, Jr. |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |
| 4,794,919 A | 1/1989 | Nilsson |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |
| 5,015,248 A | 5/1991 | Burstein et al. |
| 5,041,113 A | 8/1991 | Biedermann et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,443,516 A | 8/1995 | Albrektsson et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 5,980,575 A | 11/1999 | Albrektsson et al. |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| D449,692 S | 10/2001 | Michelson |
| 6,302,887 B1 | 10/2001 | Spranza et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,776,781 B1 | 8/2004 | Uwaydah |
| 6,863,671 B1 | 3/2005 | Strobel et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,063,701 B2 | 6/2006 | Michelson |
| 7,128,744 B2 | 10/2006 | Weaver et al. |
| D536,453 S | 2/2007 | Young et al. |
| 7,220,246 B2 | 5/2007 | Raulerson |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Wantanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady et al. |
| 7,951,178 B2 | 5/2011 | Jensen |
| 7,955,364 B2 | 6/2011 | Ziolo et al. |
| D643,121 S | 8/2011 | Milford et al. |
| D646,785 S | 10/2011 | Milford |
| 8,062,367 B2 | 11/2011 | Kirschman |
| 8,100,953 B2 | 1/2012 | White et al. |
| 8,182,485 B1 | 5/2012 | Gonzalez-Hernandez |
| 8,523,902 B2 | 9/2013 | Heaven et al. |
| 8,574,234 B2 | 11/2013 | Gonzalez-Hernandez |
| 8,597,363 B2 | 12/2013 | Liverneaux et al. |
| 8,728,126 B2 | 5/2014 | Steffen |
| 8,764,808 B2 | 7/2014 | Gonzalez-Hernandez |
| 2003/0135212 A1 | 7/2003 | Chow |
| 2003/0135216 A1 | 7/2003 | Sevrain |
| 2003/0208210 A1 | 11/2003 | Dreyfuss et al. |
| 2004/0097939 A1 | 5/2004 | Bonutti |
| 2004/0193278 A1 | 9/2004 | Maroney et al. |
| 2004/0210220 A1 | 10/2004 | Tornier |
| 2005/0004574 A1 | 1/2005 | Muckter |
| 2005/0015089 A1 | 1/2005 | Young et al. |
| 2005/0021033 A1 | 1/2005 | Zeiler et al. |
| 2005/0038513 A1 | 2/2005 | Michelson |
| 2005/0085819 A1 | 4/2005 | Ellis et al. |
| 2005/0182405 A1 | 8/2005 | Orbay et al. |
| 2005/0240187 A1 | 10/2005 | Huebner et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |

(56) References Cited

U.S. PATENT DOCUMENTS

| | | |
|---|---|---|
| 2006/0015101 A1 | 1/2006 | Warburton et al. |
| 2006/0106385 A1 | 5/2006 | Pennig |
| 2006/0161156 A1 | 7/2006 | Orbay |
| 2006/0217722 A1 | 9/2006 | Dutoit et al. |
| 2006/0235400 A1 | 10/2006 | Scheider |
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2006/0271105 A1 | 11/2006 | Foerster et al. |
| 2007/0005074 A1 | 1/2007 | Chudik |
| 2007/0016205 A1 | 1/2007 | Buetter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233114 A1 | 10/2007 | Bouman |
| 2007/0233115 A1 | 10/2007 | Sixto et al. |
| 2008/0015593 A1 | 1/2008 | Pfefferle et al. |
| 2008/0045960 A1 | 2/2008 | Bruecker et al. |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0076554 A1 | 3/2009 | Huebner et al. |
| 2009/0105838 A1 | 4/2009 | Russo et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0145339 A1 | 6/2010 | Steffen |
| 2010/0145397 A1 | 6/2010 | Overes et al. |
| 2010/0198258 A1 | 8/2010 | Heaven et al. |
| 2010/0217393 A1 | 8/2010 | Theofilos |
| 2010/0262194 A1 | 10/2010 | Wagner et al. |
| 2010/0274245 A1 | 10/2010 | Gonzalez-Hernandez |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2012/0083848 A1 | 4/2012 | Gonzalez-Hernandez |
| 2012/0109322 A1 | 5/2012 | Gonzalez-Hernandez |
| 2012/0197305 A1 | 8/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0096629 A1 | 4/2013 | Rollinghoff et al. |
| 2013/0116734 A1 | 5/2013 | Gonzalez-Hernandez |
| 2013/0289627 A1 | 10/2013 | Gonzalez-Hernandez |
| 2013/0338780 A1* | 12/2013 | Berchoux et al. ......... 623/19.11 |
| 2014/0121779 A1 | 5/2014 | Gonzalez-Hernandez |
| 2014/0172020 A1 | 6/2014 | Gonzalez-Hernandez |
| 2014/0180344 A1 | 6/2014 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 2 606 268 A1 | 5/1988 |
| EP | 0 551 588 A1 | 11/1992 |
| EP | 1 132 052 A2 | 9/2001 |
| EP | 1 468 655 A2 | 10/2004 |
| FR | 2 680 673 A1 | 3/1993 |
| JP | 4-138152 A | 5/1992 |
| WO | WO 99/38448 A1 | 8/1999 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
ACUMED; ACU-LOC Wrist Plating System; Jul. 2009; 20 pages.
ACUMED; The Mayo Clinic Congruent Elbow Plates (catalog); 2003; 19 pages.
ACUMED; The Mayo Clinic Congruent Elbow Plate System (catalog); Apr. 2006; 20 pages.
Christie, J., C.R. Howie and P.C. Armour, Fixation of displaced subcapital femoral fractures. Compression screw fixation versus double divergent pins. *J Bone Joint Surg [Br]*1988; 70-B: 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicene; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114; aulast=Guha.
Hand Innovations, LLC; DVR Anatomic, Volar Plating System; 2007; 4 pages.
Hussain M., R.N. Natarajan, A.H. Fayyazi, B.R. Braaksma, G.B. Andersson and H.S. An, *Screw angulation affects bone-screw stresses and bone graft load sharing in an anterior cervical corpectomy fusion with a rigid screw-plate construct: a finite element model study*; Spine Journal, vol. 9, Issue 12, Dec. 2009; pp. 1016-1023 (published online Oct. 12, 2009).
Lakatos R. et al.; "General pinciples of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic Loading;" 2007; 6 pages.
Robert, III, K.Q., R. Chandler, R,V, Barratta, K.A. Thomas and M.B. Harris, The effect of divergent screw placement on the initial strength of plate-to-bone fixation. *J Trauma.* Dec. 2003;55(6):1139-44.
Synthes, "Large Fragment LCP Instrument and Implant Set;" technique guide; 2003; 31 pages.
Synthes; 3.5 mm LCP Periarticular Proximal Humerus Plate; Apr. 2010; 22 pages.
Synthes; Locking Compression Plate (LCP) System (brochure); 2003; 6 pages.
Synthes, "Locking Compression Plate (LCP) System. Locking screw technology and conventional plating in one system;" 2003; 6 pages.
Synthes; Locking Compression Plate (LCP) Sytem (brochure); Jan. 2007; 6 pages.
Synthes; Modular Mini Fragment LCP System (brochure); 2007; 12 pages.
Synthes; Small Fragment Locking Compression Plate (LCP) System (brochure); 2002; 43 pages.
Written Opinion of the International Searching Authority; International Application No. PCT/US2009/036211; Sep. 23, 2010; 8 pages.
"Zimmer® Universal Locking System," The Journal of Bone and Joint Surgery, vol. 89, No. 7, Jul. 2007, 1 page.

(56) References Cited

OTHER PUBLICATIONS

Zimmer, Inc. "Zimmer® Universal Locking System," brochure (2006), 4 pages.
Zimmer, Inc.; "Zimmer Universal Locking System;" brochure; 2009, 2 pages.
Zimmer, Inc. "Zimmer Holdings to Launch Innovative Locking Plate System at Orthopaedic Trauma Association Meeting," Sep. 14, 2006; 3 pages.
Zimmer, Inc.; "Zimmer Small Fragment Universal Locking System;" Surgical Technique; 2010; 16 pages.
Zimmer; Zimmer Periarticular Plating System-Low-Profile Fixation (catalog); 2003; 8 pages.
U.S. Appl. No. 13/663,129, filed Oct. 2012, Gonzalez-Hernandez.
U.S. Appl. No. 13/840,194, filed Mar. 2013, Gonzalez-Hernandez.
U.S. Appl. No. 14/189,681, filed Feb. 2014, Gonzalez-Hernandez.
U.S. Appl. No. 14/213,310, filed Mar. 2014, Gonzalez-Hernandez.

* cited by examiner

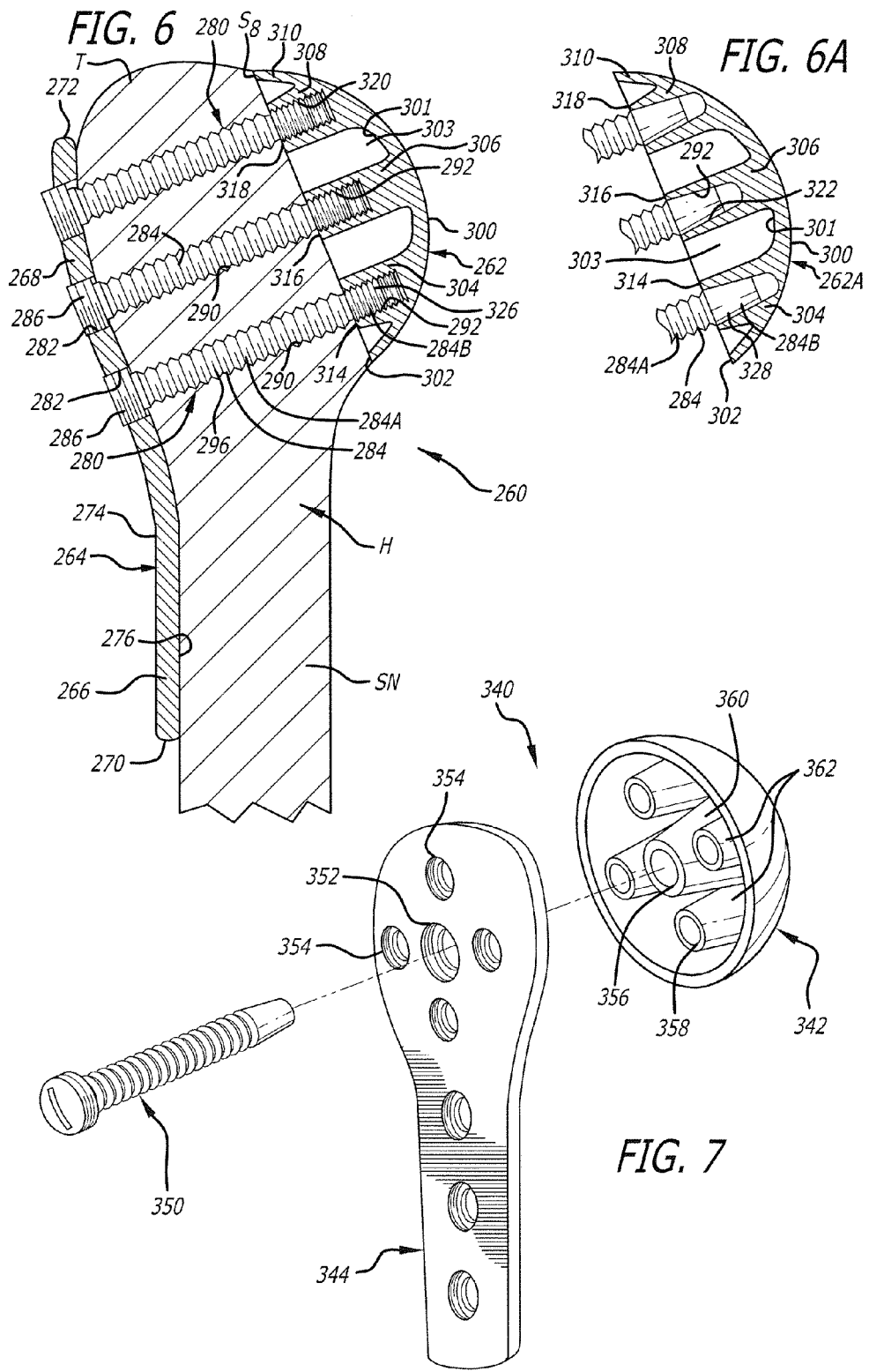

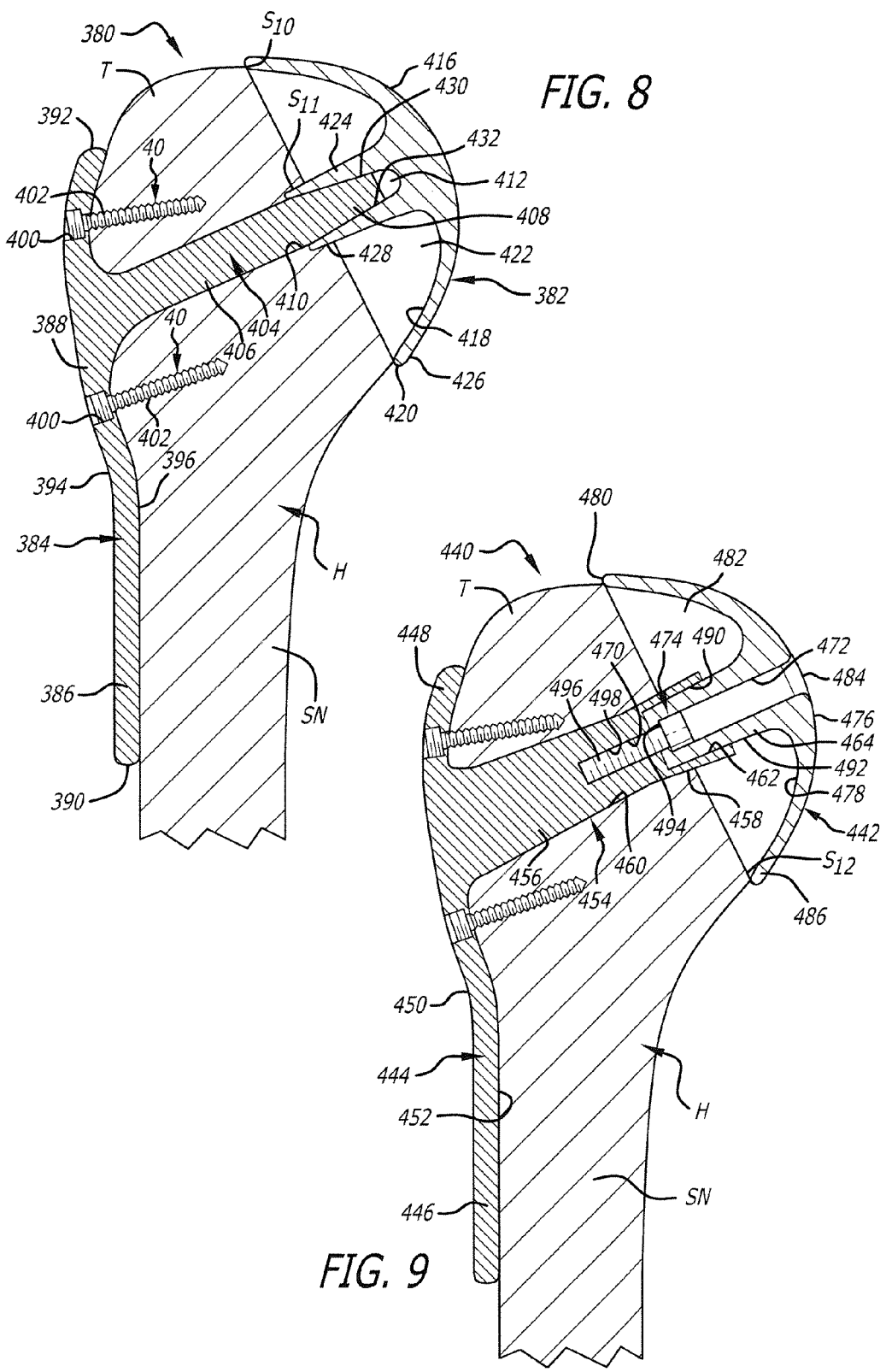

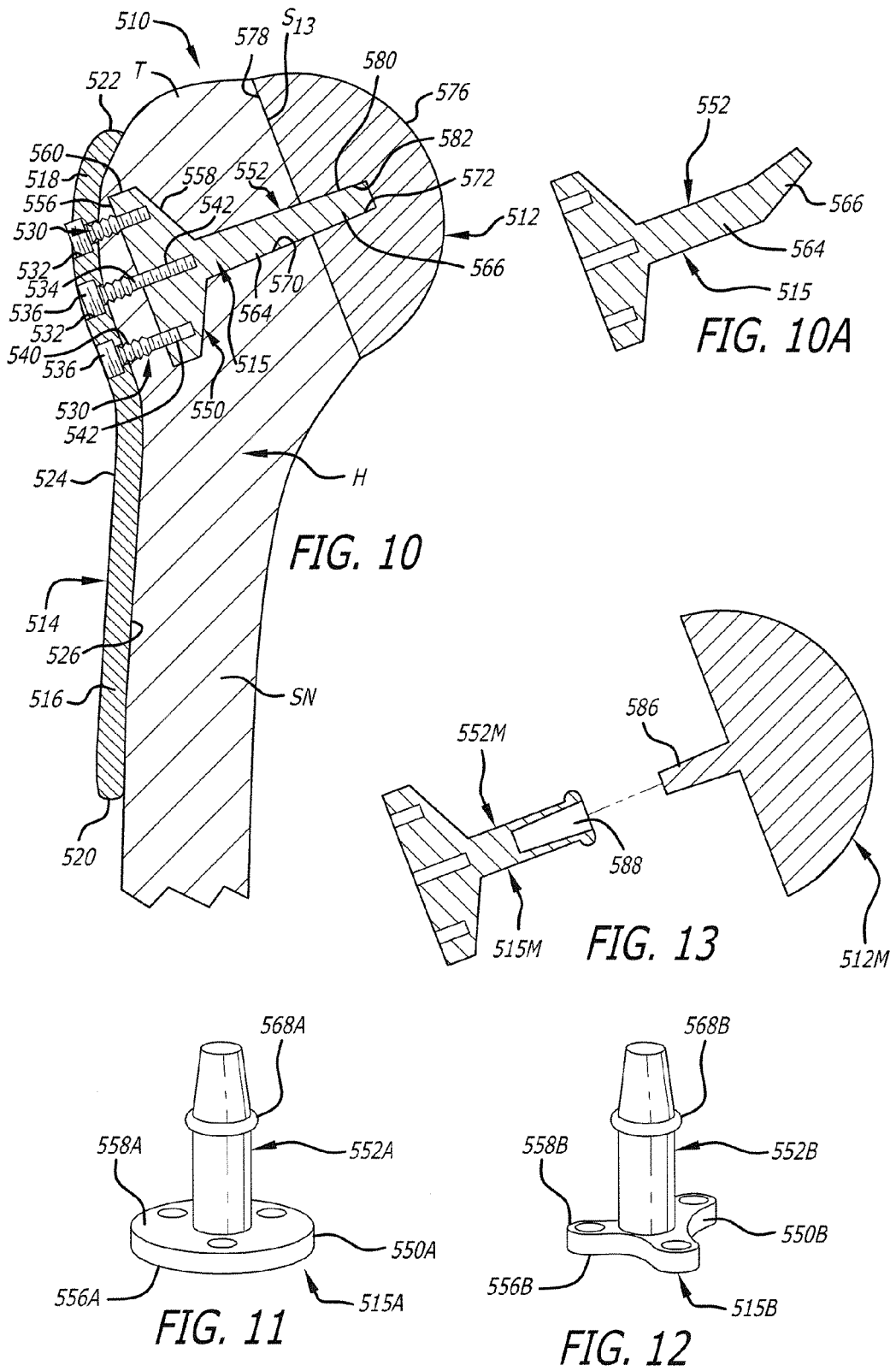

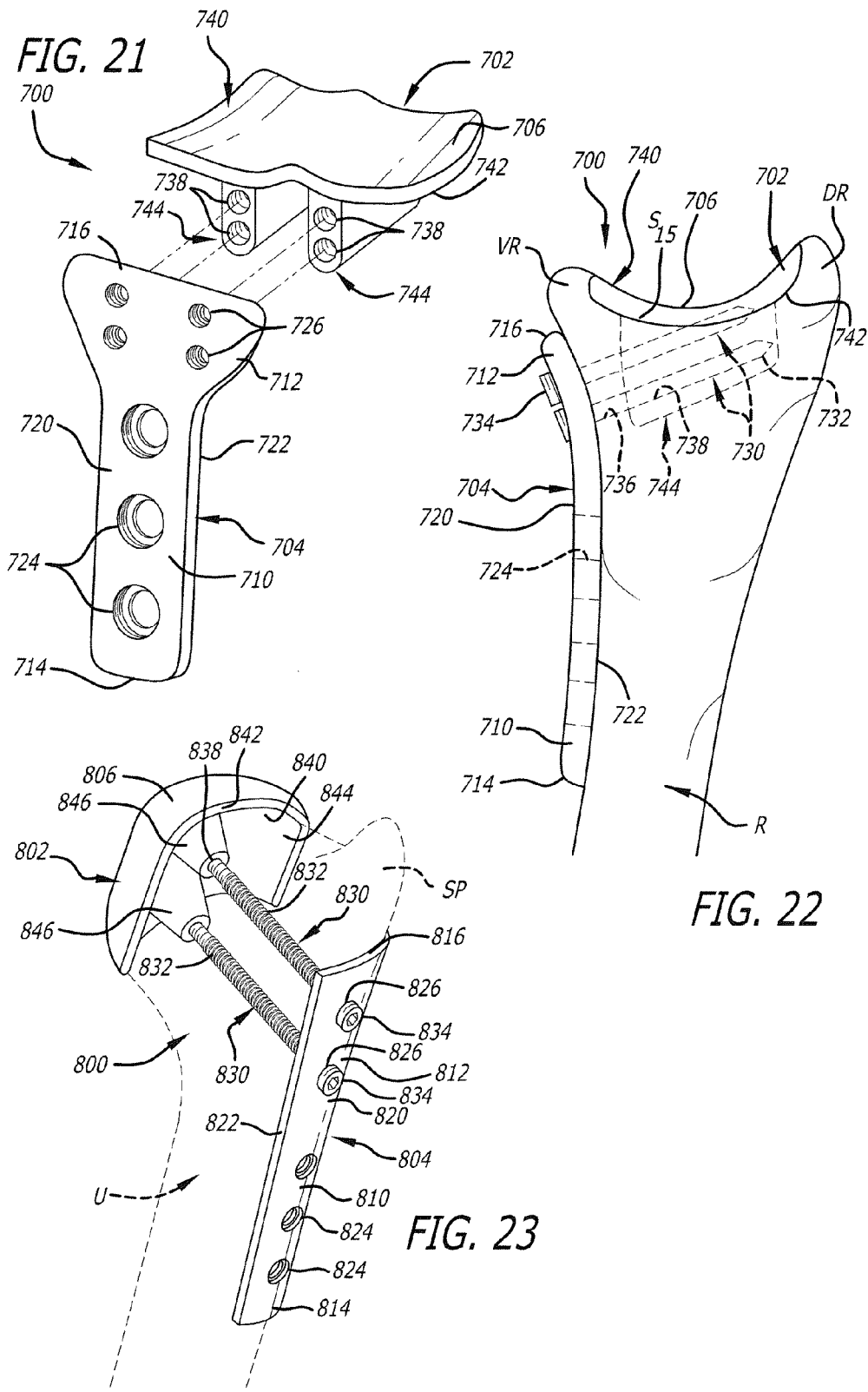

SYSTEM AND METHOD FOR FRACTURE REPLACEMENT OF COMMINUTED BONE FRACTURES OR PORTIONS THEREOF ADJACENT BONE JOINTS

The present application claims the benefit of Provisional Application No. 61/552,387, filed Oct. 27, 2011, the contents of which are incorporated herein by reference.

BACKGROUND OF THE INVENTION

1. Field of the Invention

The present invention is generally related to a medical device and method for use thereof for facilitating replacement of comminuted bone fractures. In particular, the present invention is related to a system and method for use thereof to aid in the replacement of comminuted bone fractures adjacent bone joints to restore joint viability. More specifically, the present invention relates to a system and method for use thereof for replacing comminuted bone fractures adjacent joints by providing a prosthesis to replace the fractured bone or portions of the fractured bone to facilitate restoration of movement associated with the bone joint.

2. Description of the Prior Art

Comminuted bone fractures adjacent joints oftentimes result in significant fragmentation of the bone. In fact, these types of bone fractures can often result in portions of the bone being severely fragmented. That is, the number of fragments created by these types of bone factures pose difficulties in repairing the bone. Bone plates have oftentimes been used to aid repair of the comminuted bone fractures. However, even with use of bone plates, the comminuted bone fractures may not be adequately reconstructed. For example, if severely fragmented, the proximal end portions of a humerus, the distal end portions of a radius, or the distal end portions of an ulna may not be reconstructible. As such, there is a need for a prosthesis affording replacement of the comminuted bone fractures or portions thereof to restore joint viability. The prosthesis can be used when the comminuted bone fractures need substantial support to aid repair or are irretrievably fragmented. Such a prosthesis can be used in replicating articular surfaces of the fractured bone to restore movement associated with a corresponding bone joint. For example, such a prosthesis can be configured to repair the proximal end portion of the humerus, the distal end portion of the radius, and the distal end portion of the ulna.

SUMMARY OF THE INVENTION

The present invention in one preferred embodiment contemplates a system for replacement of at least a portion of a comminuted humeral head, the system including a prosthesis and a bone plate, the prosthesis having an exterior surface being sized and shaped to approximate the surface of the at least a portion of the comminuted humeral head, the bone plate including a first surface, an opposite second surface, and at least one post formed thereon, the first surface being adapted to contact at least a portion of a humerus, the at least one post extending outwardly from the first surface, where one of the prosthesis and the at least one post includes a male component, and the other of the prosthesis and the at least one post includes a female component, the male and female components engaging one another to connect the prosthesis and the bone plate to one another.

In another preferred embodiment, the present invention contemplates a system for replacement of at least a portion of a comminuted humeral head, the system including a prosthesis having an exterior surface and at least one aperture provided therein, the exterior surface being sized and shaped to approximate the surface of the at least a portion of the comminuted humeral head; and a bone plate including a first surface, an opposite second surface, and at least one post formed thereon, the first surface being adapted to contact at least a portion of a humerus, the at least one post extending outwardly from the first surface, where, when the system is positioned with respect to the humerus, the at least one post extends through the humerus and engages the at least one aperture formed in the prosthesis to connect the prosthesis and the bone plate to one another.

In yet another preferred embodiment, the present invention contemplates a system for replacement of at least a portion of a comminuted humeral head, the system including a prosthesis having an exterior surface and at least one aperture formed therein, the exterior surface being sized and shaped to approximate the surface of the at least a portion of the comminuted humeral head; a first plate including a first surface and an opposite second surface, the first surface adapted to contact an exterior portion of a humerus; a second plate including a first surface and an opposite second surface, the first surface including at least one post extending outwardly therefrom, and the second surface being adapted to contact an interior portion of the humerus; and at least one fastener adapted to attach the first and second plates to one another and the humerus, where, when the system is position with respect to the humerus, the first plate and the second plate are attached to one another and the humerus with the at least one fastener, and the at least one post extends through the humerus and engages the at least one aperture formed in the prosthesis to connect the prosthesis and the second plate to one another.

In still another preferred embodiment, the present invention contemplates a system for replacement of at least a portion of a carpal articular surface of a radius, the system including a prosthesis having an exterior surface and at least one aperture provided therein, the exterior surface being sized and shaped to approximate the surface of the at least a portion of the carpal articular surface of the radius, and the at least one aperture of the prosthesis being adapted to receive at least one fastener therein; a bone plate including at least one opening formed therein, at least a portion of the bone plate being configured to be attached to the radius above the distal end thereof, the at least one opening of the bone plate being configured to receive the at least one fastener therethrough; and the at least one fastener having a first end for insertion through the at least one opening and into the at least one aperture, the at least one fastener being configured to secure attachment of the prosthesis and the bone plate to one another across a portion of a humerus.

In yet still another preferred embodiment, the present invention contemplates a system for replacement of at least a portion of a head of an ulna, the system including a prosthesis having an exterior surface, an interior cavity, and at least one aperture provided therein, the exterior surface being sized and shaped to approximate the surface of the at least a portion of the head of the ulna, the interior cavity configured to receive at least one of bone fragments of the ulna and a substrate therein, and the at least one aperture of the prosthesis configured to receive at least one fastener therein; a bone plate including at least one opening formed therein, at least a portion of the bone plate being configured to be attached to the ulna above the distal end thereof, the at least one opening of the bone plate being configured to receive the at least one fastener therethrough; and the at least one fastener having a first end for insertion through the at least one opening and into the at least one aperture, the at least one fastener being configured to secure attachment of the prosthesis and the bone plate to one another across a portion of a humerus.

It is understood that both the foregoing general description and the following detailed description are exemplary and explanatory only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings:

FIG. 6 depicts a partial cross-sectional elevational view of a fifth illustrative embodiment of the humeral head replacement system including a head portion and a bone plate portion attached to one another and a humerus using fasteners;

FIG. 6A depicts a partial cross-sectional fragmentary view of the head portion of the fifth illustrative embodiment of the humeral head replacement system with an alternate engagement mechanism between the head portion and the fasteners;

FIG. 7 depicts a perspective exploded-parts view of a sixth illustrative embodiment of the humeral head replacement system including a head portion and a bone plate portion attachable to one another using an oversized fastener;

FIG. 8 depicts a partial cross-sectional elevational view of a seventh illustrative embodiment of the humeral head replacement system including a head portion and a bone plate portion attached to one another and a humerus using a post formed integrally with the bone plate portion;

FIG. 9 depicts a partial cross-sectional elevational view of an eighth illustrative embodiment of the humeral head replacement system including a head portion and a bone plate portion attached to one another and a humerus using a post formed integrally with the bone plate portion and a projection formed integrally with the head portion;

FIG. 10 depicts a partial cross-sectional elevational view of a ninth illustrative embodiment of the humeral head replacement system including a head portion, a bone plate portion, and an intermediate portion, the bone plate portion and the intermediate portion being attached to one another and a humerus using fasteners, and the intermediate portion being attached to the head portion using a post formed integrally with the intermediate portion;

FIG. 10A depicts the intermediate plate portion of FIG. 10 including an angled post formed integrally therewith;

FIG. 11 depicts a perspective view of another configuration of an intermediate plate portion for use in the humeral head replacement system of FIG. 10;

FIG. 12 depicts a perspective view of yet another configuration of an intermediate plate portion for use in the humeral head replacement system of FIG. 10;

FIG. 13 depicts a partial cross-sectional elevational view of an alternate configuration of a head portion and an intermediate plate portion for use in the humeral head replacement system of FIG. 10 with an alternate engagement mechanism between the head portion and the intermediate portion;

FIG. 21 depicts a perspective exploded-parts view of an illustrative embodiment of a distal radius replacement system including a distal radius replacement portion and a bone plate portion;

FIG. 22 depicts an elevational view of the distal radius system replacement system positioned with respect to a radius, the distal radius replacement portion and the bone plate portion being attached to one another and to the radius using fasteners, and the distal radius replacement portion being depicted partially in phantom; and FIG. 23 depicts a perspective view of an illustrative embodiment of a distal ulna replacement system including a prosthetic portion and a bone plate portion attached to one another and to an ulna using fasteners, the ulna being depicted in phantom.

DETAILED DESCRIPTION OF THE PREFERRED EMBODIMENT

The systems for facilitating replacement of comminuted bone fractures or portions thereof and the methods for use thereof are depicted in the accompanying drawings. The systems of the present invention provide a prosthesis affording replacement of the comminuted bone fractures or portions thereof adjacent joints to facilitate restoration of joint viability. While the below-described systems are used in association with the proximal end portion of a humerus, the distal end portion of a radius, and a distal end portion of an ulna, the present invention is not limited thereto. That is, the systems and methods of the present invention can be configured for use elsewhere in the human body.

Systems of the present invention can be used in replacing a fractured humeral head or portions thereof at the proximal end of a humerus H that have been irretrievably fragmented. These systems are humeral head replacement systems, and various illustrative embodiments thereof are depicted in FIGS. 1-20 and are assigned numerals 20, 80, 140, 200, 260, 340, 380, 440, 510, and 600. Where possible, the components and features of the various embodiments of can be combined and used with one another. A humeral head replacement system is also disclosed in U.S. Ser. No. 13/282,810, the contents which is incorporated herein by reference.

Systems of the present invention can also be used in replacing at least portions of a fractured distal end of a radius and at least portions of a fractured distal end of an ulna. These systems are referred to as a distal radius replacement system 700 (depicted in FIGS. 21 and 22) and a distal ulna replacement system 800 (depicted in FIG. 23). A distal radius replacement system is also disclosed in U.S. Ser. No. 13/663,129 by the same inventor, being filed concurrently herewith, the contents of which is incorporated herein by reference.

Humeral head replacement systems 20, 80, 140, 200, 260, 340, 380, 440, 510, and 600, distal radius replacement system 700, and distal ulna replacement system 800 are constructed of surgical grade materials suitable for human implantation. As such, metal (such as titanium) or other artificial materials can be used for constructing the below-discussed components of humeral head replacement systems 20, 80, 140, 200, 260, 340, 380, 440, 510, and 600, distal radius replacement system 700, and distal ulna replacement system 800.

Figure 1:
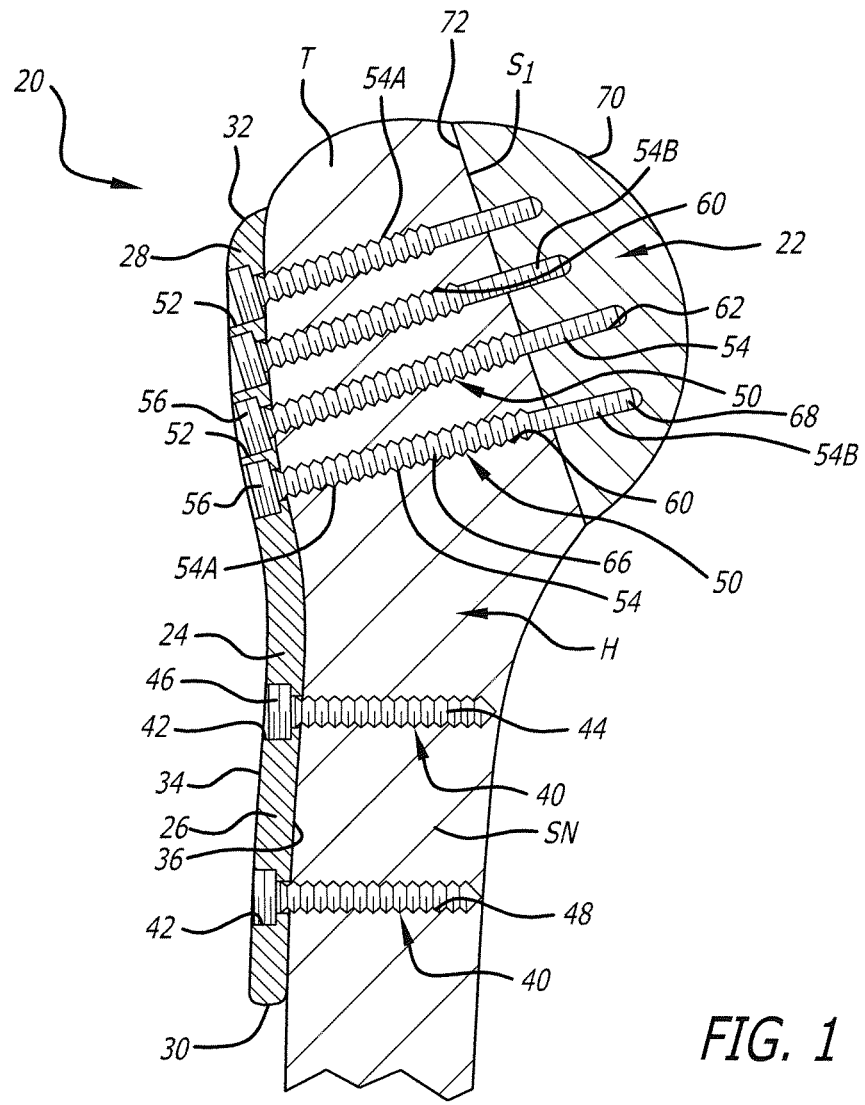
FIG. 1 depicts a partial cross-sectional elevational view of a first illustrative embodiment of a humeral head replacement system including a head portion and a bone plate portion attached to one another and a humerus using fasteners.

First humeral head replacement system 20 is depicted in FIG. 1 in position with respect to a humerus H. Humeral head replacement system 20 includes a head or prosthetic portion 22 and a bone plate portion 24. Head portion 22 serves as a prosthesis for replacement of the humeral head or portions thereof, and bone plate portion 24 is attached to humerus H to provide a rigid structure for attaching head portion 22 thereto. The rigid structure provided by the attachment of bone plate portion 24 to humerus H allows head portion 22 to be secured in position on humerus H.

As depicted in FIG. 1, bone plate portion 24 is attached to humerus H, and includes a first portion 26 and a second portion 28. As discussed below, first portion 26 is used in attaching bone plate portion 24 to humerus H at or adjacent a surgical neck SN, and second portion 28 is used in attaching bone plate portion 24 to at least one of a greater tubercle and a lesser tubercle (each generally referred to by the by character T) in the figures. Bone plate portion 24 includes a length and a longitudinal axis extending between a first end 30 and a second end 32. Furthermore, the width (i.e., the dimensions perpendicular to the length) of bone plate portion 24 can vary along the length thereof to facilitate contact with different portions of humerus H. For example, second portion 28 can be wider than first portion 26 to accommodate contact thereof with both greater and lesser tubercles T. An illustrative shape for the perimeter of bone plate portion 24 can be seen in FIG. 7.

Bone plate portion 24 includes both an upper surface 34 and a lower surface 36 extending along first and second portions 26 and 28. Lower surface 36 can be contoured to contact different portions of humerus H. That is, lower surface 36 can be shaped in accordance with portions of humerus H with which it is to be contacted. For example, lower surface 36 at first portion 28 can be contoured to contact humerus H at and/or adjacent surgical neck SN, and lower surface 36 at second portion 28 can be contoured to contact humerus H at and/or adjacent portions of greater tubercle and/or lesser tubercle T.

First portion 26 of bone plate portion 24 is configured to receive one or more fasteners (such as bone screws 40) therethrough to facilitate attachment thereof at or adjacent surgical neck SN. To that end, first portion 26 of bone plate portion 24 can include various apertures 42 (extending between upper and lower surfaces 30 and 32) for receiving bone screws 40. Bone screws 40 can be configured to facilitate engagement with bone plate portion 24 and humerus H. For example, bone screws 40 can each include a shaft 44 and a head 46 that are both threaded. Threaded shafts 44 can serve in facilitating engagement with apertures 48 formed in humerus H, and threaded heads 46 can serve in facilitating engagement with first plate portion 24 via complimentary threads (not shown) provided in apertures 36. When lower surface 36 (at first portion 26) is properly positioned with respect to humerus H, bone screws 40 can be inserted into apertures 42 and into humerus H to secure bone plate portion 24 to humerus H. Furthermore, apertures 42 can be countersunk to receive threaded heads 46, so that at least portions of threaded heads 46 ultimately can lie below upper surface 34.

Second portion 28 of bone plate portion 24 is configured to receive one or more fasteners 50 therethrough to facilitate attachment of head portion 22, bone plate portion 24, and humerus H to one another. To that end, second portion 28 can include one or more apertures 52 therethrough (extending between upper and lower surfaces 34 and 36) for receiving fasteners 50. Fasteners 50 can each include a shaft 54 and a head 56. Shafts 54 can serve in facilitating engagement with head portion 22 and humerus H, and heads 56 can serve in facilitating engagement with second portion 28. As discussed below, when lower surface 36 (at second portion 28) is properly positioned with respect to humerus H, fasteners 50 can be inserted into apertures 52, into apertures 60 formed in humerus H, and into apertures 62 formed in head portion 22. Furthermore, apertures 52 can be countersunk to receive heads 56, so that at least portions of heads 56 ultimately can lie below upper surface 34.

Four fasteners 50 and four apertures 52 are depicted in FIG. 1 arranged in alignment with one another along the longitudinal axis of bone plate portion 24. However, the number, arrangement, and spacing of apertures 52 (and hence, corresponding fasteners 50) can vary. For example, if second portion 28 is sized to contact both greater and lesser tubercles T, second portion 28 would be larger than if sized to contact only one of greater and lesser tubercles T. Thus, a larger number of apertures 52 (and corresponding fasteners 50) can be used, and apertures 52 (and corresponding fasteners 50) can be spaced farther apart from one another. Furthermore, depending on the size of second portion 28, apertures 52 (and corresponding fasteners 50) can be arranged along and/or on either side the longitudinal axis of bone plate portion 24, and, for example, can be arranged in triangular, rectangular, and diamond-shaped patterns.

The apertures 52 can be oriented to facilitate various orientations of fasteners 50 with respect to one another in three dimensions. As depicted in FIG. 1, for example, apertures 52 are oriented such that three of fasteners 50 are parallelly oriented with respect to one another, and one of fasteners 50 obliquely oriented with respect to the other three fasteners 50. Alternatively, apertures 52 can be oriented so that two or more of fasteners 50 are parallelly oriented with respect to one another, and/or be oriented so that two or more of fasteners 50 are obliquely oriented with respect to one another. To illustrate, apertures 52 can allow each of fasteners 50 to be parallelly oriented relative to one another, or can allow each of fasteners 50 to be obliquely oriented relative to one another. The parallel and oblique orientations can be into and out of the page defined by FIG. 1.

Shafts 54 and heads 56 of fasteners 50 (and the shafts and heads of similar fasteners discussed below) can have different sizes and shapes (e.g., be configured to have cylindrical or frusto-conical shaped portions), and have regular roughened or rough surfaces (hereinafter regular roughened surfaces), irregular roughened or rough surfaces (hereinafter irregular roughened surfaces), and/or smoothened or smooth surfaces (hereinafter smoothened surfaces) provided on the cylindrical or frusto-conical shaped portions. The regular roughened surfaces are repeating patterns of surface protrusions or indentations (such as threads, ratchets, or similar structures), and the irregular roughened surfaces (such as barbs or similar structures) are non-repeating surface protrusions or indentations. The regular roughened surfaces, the irregular roughened surfaces, and/or the smoothened surfaces can serve in preventing withdrawal of fasteners 50 from the components of humeral head replacement system 20 and humerus H.

To illustrate, regular roughened surfaces provided on shafts 54 can be used for complimentary engagement or interference, press, or friction fits with the components of humeral head replacement system 20 or portions of humerus H to which shafts 54 are contacted to prevent withdrawal therefrom. If complimentary engagement surfaces are provided in the components or humerus H, regular roughened surfaces of shafts 54 can complimentarily interface with the complimentary engagement surfaces. For example, threads/ratchets formed on shafts 54 can engage corresponding threads/ratchets provided in apertures formed in the components to which shafts 54 are engaged to prevent withdrawal of fasteners 50. If no complimentary engagement surfaces are provided in the components or humerus H, the regular roughened surfaces can be used in deforming the components or humerus H to provide an interference, press, or friction fit therebetween. For example, ratchets formed on shafts 54 can engage, and, in doing so, deform apertures formed in the bone of humerus H to prevent withdrawn of fasteners 50.

In addition, to illustrate, irregular roughened surfaces provided on shafts 54 can be used in deforming the components of humeral head replacement system 20 and humerus H to provide an interference, press, and/or friction fit therebetween. For example, barbs formed on shafts 54 can engage, and, in doing so, deform apertures formed in the bone of humerus H. The contact of the barbs within these apertures in the humerus H afforded by such deformation would serve in preventing withdrawal of fasteners 50 therefrom.

Additionally, to illustrate, smoothened surfaces provided on shafts 54 can be used in deforming the components of the humeral head replacement system 20 and humerus H to provide an interference, press, and/or friction fit therebetween. For example, smoothened surfaces (such as tapered or conical surfaces) formed on shafts 54 can engage and deform apertures formed in the components. The compression and friction forces applied to the smoothened surfaces within the apertures would serve in preventing withdrawal of fasteners 50 therefrom.

Like threaded heads 46 (of bone screws 40), heads 56 can, as discussed above, be threaded to serve in facilitating engagement with complimentary threads (not shown) provided in apertures 52. Furthermore, shafts 54 can each include a first portion 54A and a second portion 54B. First portions 54A can be used in engaging apertures 60 formed through humerus H, and second portions 54B can be used in engaging corresponding surfaces of apertures 62 formed in head portion 22. First and second portions 54A and 54B can be configured to have identical or different shapes, lengths, and widths, and can include the above-discussed regular roughened surfaces, irregular roughened surfaces, and/or smoothened surfaces.

The connection between head portion 22 and bone plate portion 24 afforded by fasteners 50 serves in maintaining the positions of the components of humeral head replacement system 20 relative to humerus H. However, the configuration of fasteners 50 can also serve in maintaining the position of humeral head replacement system 20 relative to humerus H. The regular or irregular roughened surfaces can serve in fixing fasteners 50 relative to humerus H. For example, if first portions 54A include threads/ratchets 66, threads/ratchets 66 of first portions 54A would engage apertures 60 to resist linear rearward movement (or backing out) of fasteners 50 from humerus H.

Head portion 22, as depicted in FIG. 1, is generally shaped as a substantially solid spherical cap. Head portion 22 includes an articular surface 70 and a bone-contacting surface 72. Articular surface 70 is substantially similar to the shape of the articular surface of the humeral head (or portions thereof) for which it is used in replacing. Furthermore, bone-contacting surface 72 contacts humerus H along surface $S_1$ and apertures 62 (for receiving second portions 54B) extend through bone-contacting surface 72 into head portion 22. As depicted in FIG. 1, bone-contacting surface 72 is substantially flat. However, bone-contacting surface 72 can be concave, convex, or undulating with various concavities and convexities to accommodate the shape of surface $S_1$. Surface $S_1$ can be prepared to interface with the shape of bone-contacting surface 72.

Depending, as discussed above, on whether second portions 54B have regular roughened surfaces, irregular roughened surfaces, and/or smoothened surfaces, engagement of fasteners 50 to head portion 22 would be different. For example, if second portions 54B include threads/ratchets 68, second portions 54B can engage (via complimentary structures formed in and/or via interference, press, and/or friction fits with) apertures 62. Furthermore, if second portions 54B have smoothened surfaces, second portions 54B can engage (via interference, press, and/or friction fits) surfaces formed in apertures 62 These interactions serve in attaching fasteners 50 (and hence, bone plate portion 24) to head portion 22.

If threads/ratchets are used for attachment, configurations of threads/ratchets 66 and 68 of first and second portions 54A and 54B, respectively, can be different to accommodate their respective uses. For example, first portion 54A can have coarser threads for engagement with humerus H, and second portion 54B can have finer threads for engagement to head portion 22. Furthermore, first portion 54A can have larger ratchets for engagement with humerus H, and second portion 54B can have smaller ratchets for engagement with head portion 22.

Figure 2:
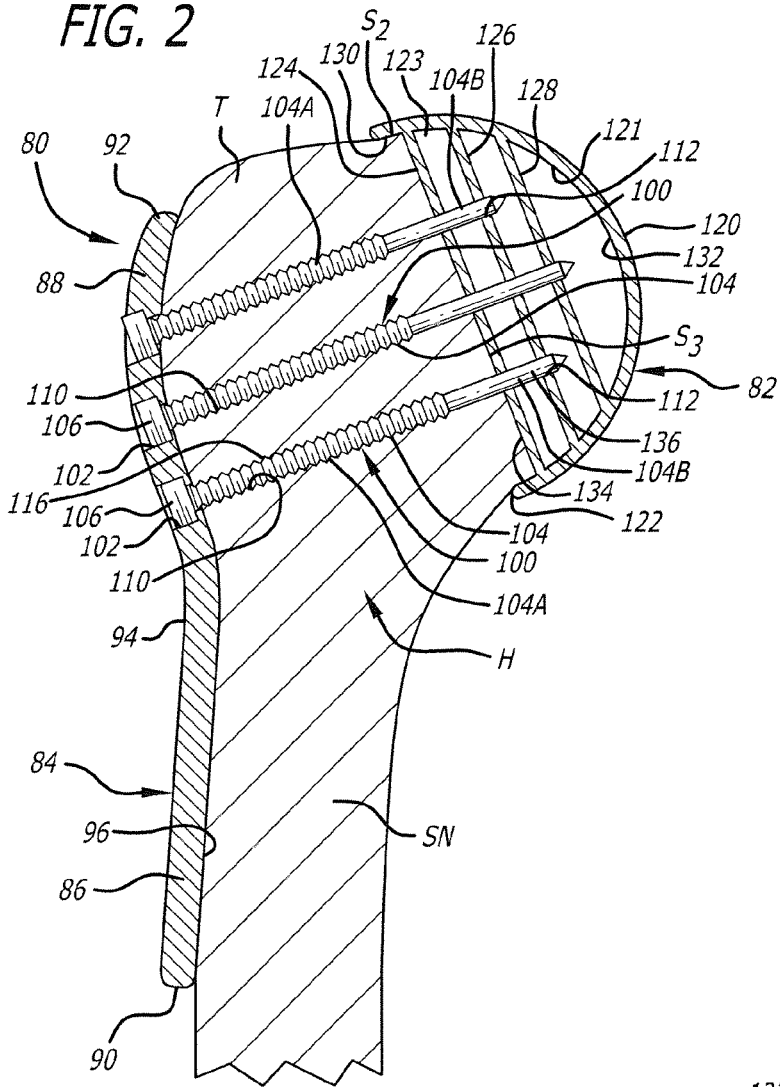
FIG. 2 depicts a partial cross-sectional elevational view of a second illustrative embodiment of the humeral head replacement system including a head portion and a bone plate portion attached to one another and a humerus using fasteners.

Second humeral head replacement system 80 is depicted in FIG. 2 in position with respect to humerus H. Humeral head replacement system 80 includes a head or prosthetic portion 82 (also depicted in FIG. 3) and a bone plate portion 84. Like head portion 22, head portion 82 serves as a prosthesis for replacement of humeral head or portions thereof, and, like bone plate portion 24, bone plate portion 84 is attached to humerus H to provide a rigid structure for attaching head portion 82 thereto. The rigid structure provided by the attachment of bone plate portion 84 to humerus H allows head portion 82 to be secured in position on humerus H.

As depicted in FIG. 2, bone plate portion 84 is attached to humerus H, and includes a first portion 86 and a second portion 88. First portion 86 is used in attaching bone plate portion 84 to humerus H at or adjacent surgical neck SN, and second portion 88 is used in attaching bone plate portion 84 to at least one of greater or lesser tubercles T. Bone plate portion 84 includes a length and a longitudinal axis extending between a first end 90 and a second end 92. Furthermore, like the width of bone plate portion 24, the width (i.e., the dimensions perpendicular to the length) of bone plate portion 84 can vary along the length thereof to facilitate contact with different portions of humerus H. For example, second portion 88 can be wider than first portion 86 to accommodate contact thereof with both of greater and lesser tubercles T. An illustrative shape for the perimeter of bone plate portion 84 can be seen in FIG. 7.

Like bone plate portion 24, bone plate portion 84 includes both an upper surface 94 and a lower surface 96 extending along first and second portions 86 and 88. Like lower surface 36 of first and second portions 26 and 28, lower surface 96 of first and second portions 86 and 88 can be contoured to contact different portions of humerus H.

Furthermore, although not depicted in FIG. 2, first portion 86 can include apertures (similar to apertures 42) extending between upper and lower surfaces 94 and 96 that are configured for receiving fasteners such as bone screws 40. Like first portion 26 of bone plate portion 24, first portion 86 of bone plate portion 84 can be attached at or adjacent surgical neck SN using bone screws 40. Bone screws 40 can engage the apertures formed in first portion 86, as well as apertures (not shown) formed in humerus H.

Second portion 88 of bone plate portion 84 is configured to receive one or more fasteners 100 therethrough to facilitate attachment of head portion 82, bone plate portion 84, and humerus H to one another. To that end, second portion 88 can include one or more apertures 102 therethrough (extending between upper and lower surfaces 94 and 96) for receiving fasteners 100. Fasteners 100 can each include a shaft 104 and a head 106. Shafts 104 can serve in facilitating engagement with head portion 82 and humerus H, and heads 106 can serve in facilitating engagement with second portion 88. When lower surface 96 (at second portion 88) is properly positioned with respect to humerus H, fasteners 100 can be inserted into apertures 102, into apertures 110 formed in humerus H, and into apertures 112 formed in head portion 82. Furthermore, apertures 102 can be countersunk to receive heads 106, so that at least portions of heads 106 ultimately can lie below upper surface 94.

Three fasteners 100 and three apertures 102 are depicted in FIG. 2 arranged to have a generally parallel orientation with respect to one another. Fasteners 100 and apertures 102 are spaced along the longitudinal axis of bone plate portion 84. Furthermore, in similar fashion to apertures 52 (and corresponding fasteners 50) of first humeral head replacement system 20, the number, arrangement, spacing, and orientation of apertures 102 (and hence, corresponding fasteners 100) can vary further. Like with first humeral head replacement system 20, these variations (such as positioning thereof on either side of the longitudinal axis and the pattern formed thereby) for apertures 102 (and corresponding fasteners 100) can occur because second portion 88 is sized to contact varying portions of humerus H, and the desire to have the fasteners 100 parallelly or obliquely oriented with respect to one another.

Like shafts 54 and heads 56, shafts 104 and heads 106 can be configured to have cylindrical or frusto-conical shaped portions, and have regular roughened surfaces, irregular roughened surfaces, and/or smoothened surfaces provided on the cylindrical or frusto-conical shaped portions. Furthermore, like shafts 54, shafts 104 can include first portions 104A used in engaging apertures 110 formed through humerus H, and second portions 104B used in engaging corresponding surfaces of apertures 112 formed in head portion 82. First and second portions 104A and 104B can be configured to have identical or different shapes, lengths, and widths, and can include the above-discussed regular roughened surfaces, irregular roughened surfaces, and/or smoothened surfaces.

The connection between head portion 82 and bone plate portion 84 afforded by fasteners 100 serves in maintaining the positions of the components of humeral head replacement system 80 relative to humerus H. Indeed, portions of humerus H are clamped between head portion 82 and bone plate portion 84. Furthermore, in addition to the connection between head portion 82 and bone plate portion 84 afforded thereby, the configuration of fasteners 100 can serve in resisting movement (and hence, maintaining the position) of the components of humeral head replacement system 80 relative to humerus H. That is, the regular or irregular roughened surfaces formed on shafts 104 can serve in fixing fasteners 100 relative to humerus H. For example, if first portions 104A include threads/ratchets 116, threads/ratchets 116 would resist linear rearward movement (or backing out) of fasteners 100 from apertures 110.

Figure 3:
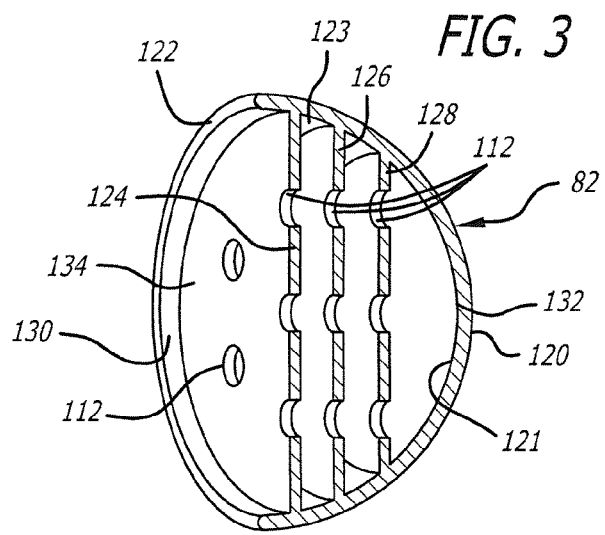
FIG. 3 depicts a partial cross-sectional perspective view of the head portion depicted in FIG. 2.

Head portion 82, as depicted in FIGS. 2 and 3, is generally shaped as a substantially semi-hollow spherical cap. Head portion 82 includes an articular surface 120, an interior surface 121, a bone-contacting rim 122, an interior cavity 123 delineated at least in part by interior surface 121 and bone-contacting rim 122, and slats 124, 126, and 128. Articular surface 120 is substantially similar to the shape of the articular surface of the humeral head (or portions thereof) for which it is used in replacing. Furthermore, the thickness of head portion 82 between articular and interior surfaces 120 and 121, as well as the thicknesses of slats 124, 126, and 128, can vary.

As depicted in FIG. 2, bone-contacting rim 122 is formed at a base 130 of head portion 82, and contacts surface $S_2$ of humerus H. Bone-contacting rim 122 can be configured to accommodate the shape of surface $S_2$, and surface $S_2$ can be prepared to interface with the shape of bone-contacting rim 122. Furthermore, slats 124, 126, and 128 include apertures 112 for receiving fasteners 100. Slats 124, 126, and 128 extend between portions of interior surface 121 in interior cavity 123, and are positioned at intervals between base 130 and apex 132 of head portion 82. A substrate (not shown) can be positioned between slats 124, 126, and 128 to reinforce head portion 82. For example, polymeric material such as, polyethylene can be provided in the space between slats 124, 126, and 128.

Apertures 112 formed in slats 124, 126, and 128 can be aligned with one another to facilitate receipt of fasteners 100. That is, each of slats 124, 126, and 128 includes one of apertures 112 for receipt of a corresponding one of fasteners 100. Apertures 112 can be aligned to afford different orientations of fasteners 100 with respect to slats 124, 126, and 128. For example, as depicted in FIGS. 2 and 3, apertures 112 (corresponding to each of fasteners 100) are aligned so that fasteners 100 are perpendicularly angled with respect to slats 124, 126, and 128. However, apertures 112 (corresponding to each of fasteners 100) can be aligned so that fasteners 100 are obliquely angled with respect to slats 124, 126, and 128. If the substrate is provided between slats 124, 126, and 128, apertures 112 would also be extended through the substrate.

As depicted in FIGS. 2 and 3, slats 124, 126, and 128 decrease in size from bone-contacting rim 122 to apex 132. Slats 124, 126, and 128 depicted in FIGS. 2 and 3 also have generally parallel orientations with respect to one another and are spaced equally apart from one another. However, slats 124, 126, and 128 can have angled orientations with respect to one another, and can have concave surfaces and/or convex surfaces, or include undulating surfaces with various concavities and convexities. Furthermore, slat 124 can include a bone-contacting surface 134 for engaging humerus H at surface $S_3$. Like bone-contacting surface 72 of head portion 22, bone-contacting surface 134 can be concave, convex, or undulating with various concavities and convexities to accommodate the shaped of surface $S_3$. Furthermore, surface $S_3$ can be prepared to interface with the shape of bone-contacting surface 134.

Depending on whether second portions 104B have regular roughened surfaces, irregular roughened surfaces, and/or smoothened surfaces, engagement of fasteners 100 to head portion 82 would be different. For example, if second portions 104B include threads/ratchets, second portions 104B can engage (via complimentary structures formed in and/or via interference, press, and/or friction fits with) apertures 112. Furthermore, if second portions 104B have smoothened surfaces 136, second portions 104B can engage (via interference, press, and/or friction fits) surfaces formed in apertures 112. The interactions afforded by the complimentary structures and interference, press, and/or friction fits serve in attaching fasteners 100 to head portion 82 by resisting linear movement (or backing out) of fasteners 100 from head portion 82 after insertion into apertures 112.

Figures 4, 5:
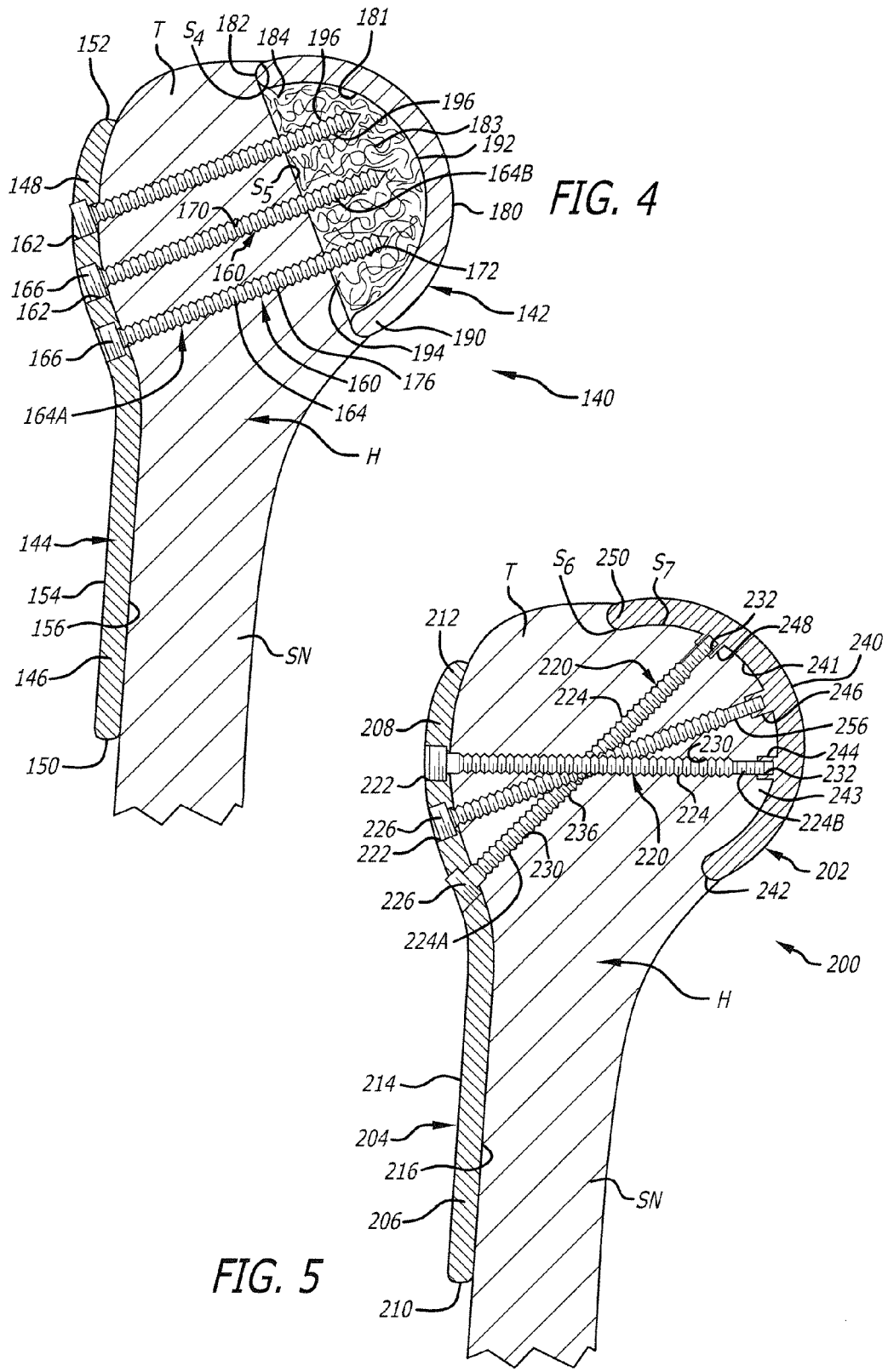
FIG. 4 depicts a partial cross-sectional elevational view of a third illustrative embodiment of the humeral head replacement system including a head portion and a bone plate portion attached to one another and a humerus using fasteners.
FIG. 5 depicts a partial cross-sectional elevational view of a fourth illustrative embodiment of the humeral head replacement system including a head portion and a bone plate portion attached to one another and a humerus using fasteners.

Third humeral head replacement system 140 is depicted in FIG. 4 in position with respect to humerus H. Humeral head replacement system 140 includes a head or prosthetic portion 142 and a bone plate portion 144. Like head portion 22, head portion 142 serves as a prosthesis for replacement of the humeral head or portions thereof, and, like bone plate portion 24, bone plate portion 144 is attached to humerus H to provide a rigid structure for attaching head portion 142 thereto. The rigid structure provided by the attachment of bone plate portion 142 to humerus H allows head portion 142 to be secured in position on humerus H.

As depicted in FIG. 4, bone plate portion 144 is attached to humerus H, and includes a first portion 146 and a second portion 148. First portion 146 is used in attaching bone plate portion 144 to humerus H at or adjacent surgical neck SN, and second portion 148 is used in attaching bone plate portion 144 to at least one of greater or lesser tubercles T. Bone plate portion 144 includes a length and a longitudinal axis extending between a first end 150 and a second end 152. Furthermore, like the width of bone plate portion 24, the width (i.e., the dimensions perpendicular to the length) of bone plate portion 144 can vary along the length thereof to facilitate contact with different portions of humerus H. For example, second portion 148 can be wider than first portion 146 to accommodate contact thereof with both of greater and lesser tubercles T. An illustrative shape for the perimeter of bone plate portion 144 can be seen in FIG. 7.

Like bone plate portion 24, bone plate portion 144 includes both an upper surface 154 and a lower surface 156 extending along first and second portions 146 and 148.

Like lower surface 36 of first and second portions 26 and 28, lower surface 156 of first and second portions 146 and 148 can be contoured to contact different portions of humerus H.

Furthermore, although not depicted in FIG. 4, first portion 146 can include apertures (similar to apertures 42) extending between upper and lower surfaces 154 and 156 that are configured for receiving fasteners such as bone screws 40. Like first portion 26 of bone plate portion 24, first portion 146 of bone plate portion 144 can be attached at or adjacent surgical neck SN using bone screws 40. Bone screws 40 can engage the apertures formed in the first portion 146, as well as apertures (not shown) formed in humerus H.

Second portion 148 of bone plate portion 144 is configured to receive one or more fasteners 160 therethrough to facilitate attachment of head portion 142, bone plate portion 144, and humerus H to one another. To that end, second portion 148 can include one or more apertures 162 therethrough (extending between upper and lower surfaces 154 and 156) for receiving fasteners 160. Fasteners 160 can each include a shaft 164 and a head 166. Shafts 164 can serve in facilitating engagement with head portion 142 and humerus H, and heads 166 can serve in facilitating engagement with second portion 148. When lower surface 156 (at second portion 148) is properly positioned with respect to humerus H, fasteners 160 can be inserted into apertures 162, into apertures 170 formed in humerus H, and into apertures 172 formed in head portion 142. Furthermore, apertures 162 can be countersunk to receive heads 166, so that at least portions of heads 166 ultimately can lie below upper surface 154.

Three fasteners 160 and three apertures 162 are depicted in FIG. 4 arranged to have a generally parallel orientation with respect to one another. Fasteners 160 and apertures 162 are spaced along the longitudinal axis of bone plate portion 144. Furthermore, in similar fashion to apertures 52 (and corresponding fasteners 50) of first humeral head replacement system 20, the number, arrangement, spacing, and orientation of apertures 162 (and hence, corresponding fasteners 160) can vary further. Like with first humeral head replacement system 20, these variations (such as the positioning thereof on either side of the longitudinal axis and pattern formed thereby) for apertures 162 (and corresponding fasteners 160) can occur because second portion 148 is sized to contact varying portions of humerus H, and the desire to have the fasteners 160 parallelly or obliquely oriented with respect to one another.

Like shafts 54 and heads 56, shafts 164 and heads 166 can be configured to have cylindrical or frusta-conical shaped portions, and have regular roughened surfaces, irregular roughened surfaces, and/or smoothened surfaces provided on the cylindrical or frusto-conical shaped portions. Furthermore, like shafts 54, shafts 164 can include first portions 164A used in engaging apertures 170 formed through humerus H, and second portions 164B used in engaging corresponding surfaces of apertures 172 formed in head portion 142. First and second portions 164A and 164B can be configured to have identical or different shapes, lengths, and widths, and can include the above-discussed regular roughened surfaces, irregular roughened surfaces, and/or smoothened surfaces.

The connection between head portion 142 and bone plate portion 144 afforded by fasteners 160 serves in maintaining the positions of the components of humeral head replacement system 140 relative to humerus H. Indeed, portions of humerus H are clamped between head portion 142 and bone plate portion 144. Furthermore, in addition to the connection between head portion 142 and bone plate portion 144 afforded thereby, the configuration of fasteners 160 can serve in resisting movement (and hence, maintaining the position) of the components of humeral head replacement system 140 relative to humerus H. That is, the regular or irregular roughened surfaces formed on shafts 164 can serve in fixing fasteners 160 relative to humerus H. For example, if first portions 164A include threads/ratchets 176, threads/ratchets 176 would resist linear rearward movement (or backing out) of fasteners 160 from apertures 170.

Head portion 142, as depicted in FIG. 4, is generally shaped as a substantially semi-hollow spherical cap. Head portion 142 includes an articular surface 180, an interior surface 181, a bone-contacting rim 182, an interior cavity 183 delineated at least in part by interior surface 181 and bone-contacting rim 182, and a substrate 184 provided in interior cavity 183. Articular surface 180 is substantially similar to the shape of the articular surface of the humeral head (or portions thereof) for which it is used in replacing. The thickness of head portion 142 between articular and interior surfaces 180 and 181 can vary. As depicted in FIG. 4, bone-contacting rim 182 is formed at a base 190 of head portion 142, and contacts surface $S_4$ of humerus H. Bone-contacting rim 182 can be configured to accommodate the shape of surface $S_4$, and surface $S_4$ can be prepared to interface with the shape of bone-contacting rim 182.

Substrate 184 can be formed from a material other than the material used in forming the remainder of head portion 142. For example, as depicted in FIG. 4, substrate 184 can be lattice structure such as a regular or irregular wire mesh material. Substrate 184 can also be a solid polymeric material such as, for example, polyethylene. Substrate 184 can be attached, adhered, and/or fastened to interior surface 181, can extend from base 190 to apex 192 of head portion 142, and can be used to reinforce head portion 142. Furthermore, apertures 172 are formed in substrate 184. Apertures 172 can be formed prior to receipt of fasteners 160 therein, or can be formed by the force of penetration of fasteners 160. Forming apertures 172 by the force of penetration significantly diminishes the need for accurately targeting fasteners to engage the components of humeral head replacement system 140. Furthermore, substrate 184 can include a bone-contacting surface 194 for engaging humerus H at surface $S_5$. Like bone-contacting surface 72 of head portion 22, bone-contacting surface 194 can be concave, convex, or undulating with various concavities and convexities to accommodate the shape of surface $S_5$. Furthermore, surface $S_5$ can be prepared to interface with the shape of bone-contacting surface 194. If substrate 184 is a wire mesh material, surface $S_5$ can be prepared to facilitate growth of bone into the wire mesh material.

Depending on whether apertures 172 are formed prior to receipt of fasteners 160 or formed by the force of penetration of fasteners 160, and whether second portions 164B have regular roughened surfaces (such as threads/ratchets 196 depicted in FIG. 4), irregular roughened surfaces, and/or smoothened surfaces, engagement of fasteners 160 to head portion 142 would be different.

For example, if apertures 172 are formed prior to receipt of fasteners 160, second portions 164B can include regular roughened surfaces (such as threads/ratchets 196) used for engaging complimentary structures formed in apertures 172 or engaging (via interference, press, and/or friction fits) surfaces formed in apertures 172. Furthermore, if apertures 172 are formed by the force of penetration of fasteners 172, second portions 164B can include regular roughened surfaces (such as threads/ratchets 196) or irregular roughened surfaces—the regular and irregular roughened surfaces can be used to facilitate penetration of fasteners 160 into and interference, press, and/or friction fits with substrate 184. The interactions afforded by the complimentary structures and the interference, press, and/or friction fits serve in attaching fasteners 160 to head portion 142 by resisting linear movement (or backing out) of fasteners 160 from head portion 142 after insertion into apertures 112.

Fourth humeral head replacement system 200 is depicted in FIG. 5 in position with respect to humerus H. Humeral head replacement system 200 includes a head or prosthetic portion 202 and a bone plate portion 204. Like head portion 22, head portion 202 serves as a prosthesis for replacement of the humeral head or portions thereof, and, like bone plate portion 24, bone plate portion 204 is attached to humerus H to provide a rigid structure for attaching head portion 202 thereto. The rigid structure provided by the attachment of bone plate portion 204 to the humerus H allows head portion 202 to be secured in position on humerus H.

As depicted in FIG. 5, bone plate portion 204 is attached to humerus H, and includes a first portion 206 and a second portion 208. First portion 206 is used in attaching bone plate portion 204 to humerus H at or adjacent surgical neck SN, and second portion 208 is used in attaching bone plate portion 204 to at least one of greater or lesser tubercles T. Bone plate portion 204 includes a length and a longitudinal axis extending between a first end 210 and a second end 212. Furthermore, like the width of bone plate portion 24, the width (i.e., the dimensions perpendicular to the length) of bone plate portion 204 can vary along the length thereof to facilitate contact with different portions of humerus H. For example, second portion 208 can be wider than first portion 206 to accommodate contact thereof with both of greater and lesser tubercles T. An illustrative shape for the perimeter of bone plate portion 204 can be seen in FIG. 7.

Like bone plate portion 24, bone plate portion 204 includes both an upper surface 214 and a lower surface 216 extending along first and second portions 206 and 208. Like lower surface 36 of first and second portions 26 and 28, lower surface 216 of first and second portions 206 and 208 can be contoured to contact different portions of humerus H.

Furthermore, although not depicted in FIG. 5, first portion 206 can include apertures (similar to apertures 42) extending between upper and lower surfaces 214 and 216 that are configured for receiving fasteners such as bone screws 40. Like first portion 26 of bone plate portion 24, first portion 206 of bone plate portion 204 can be attached at or adjacent surgical neck SN using bone screws 40. Bone screws 40 can engage the apertures formed in first portion 206, as well as apertures (not shown) formed in humerus H.

Second portion 208 of bone plate portion 204 is configured to receive one or more fasteners 220 therethrough to facilitate attachment of head portion 202, bone plate portion 204, and humerus H to one another. To that end, second portion 208 can include one or more apertures 222 therethrough (extending between upper and lower surfaces 214 and 216) for receiving fasteners 220. Fasteners 220 can each include a shaft 224 and a head 226. Shafts 224 can serve in facilitating engagement with head portion 202 and humerus H, and heads 226 can serve in facilitating engagement with second portion 208. When lower surface 216 (at second portion 208) is properly positioned with respect to humerus H, fasteners 220 can be inserted into apertures 222, into apertures 230 formed in humerus H, and into apertures 232 formed in head portion 202. Furthermore, apertures 222 can be countersunk to receive heads 226, so that at least portions of heads 226 ultimately can lie below upper surface 214.

Three fasteners 220 and three apertures 222 are depicted in FIG. 5 arranged to have oblique orientations with respect to one another. Fasteners 220 and apertures 222 are spaced along the longitudinal axis of bone plate portion 204. However, given the spacing thereof along the longitudinal axis of bone plate 204, apertures 222 would be oriented so that fasteners 220 are also angled differently into and out of the page defined by FIG. 5, so as to avoid interference with one another. As such, given such orientations of apertures 222, the fasteners 220 can have a crisscrossed orientation as depicted in FIG. 5.

Furthermore, in similar fashion to apertures 52 (and corresponding fasteners 50) of first humeral head replacement system 20, the number, arrangement, spacing, and orientation of apertures 222 (and hence, corresponding fasteners 220) can vary further.

Like with first humeral head replacement system 20, these variations (such as the positioning thereof on either side of the longitudinal axis and pattern formed thereby) for apertures 222 (and corresponding fasteners 220) can occur because second portion 208 is sized to contact varying portions of humerus H, and the desire to have the fasteners 220 parallelly or obliquely oriented with respect to one another.

Like shafts 54 and heads 56, shafts 224 and heads 226 can be configured to have cylindrical or frusto-conical shaped portions, and have regular roughened surfaces, irregular roughened surfaces, and/or smoothened surfaces provided on the cylindrical or frusto-conical shaped portions. Furthermore, like shafts 54, shafts 224 can include first portions 224A used in engaging apertures 230 formed through humerus H, and second portions 224B used in engaging corresponding surfaces of apertures 232 formed in head portion 202. First and second portions 224A and 224B can be configured to have identical or different shapes, lengths, and widths, and can include the above-discussed regular roughened surfaces, irregular roughened surfaces, and/or smoothened surfaces.

The connection between head portion 202 and bone plate portion 204 afforded by fasteners 220 serves in maintaining the positions of the components of humeral head replacement system 200 relative to humerus H. Indeed, portions of humerus H are clamped between head portion 202 and bone plate portion 204. Furthermore, in addition to the connection between head portion 202 and bone plate portion 204 afforded thereby, the configuration of fasteners 220 can serve in resisting movement (and hence, maintaining the position) of the components of humeral head replacement system 200 relative to humerus H. That is, the regular or irregular roughened surfaces formed on shafts 224 can serve in fixing fasteners 220 relative to humerus H. For example, if first portions 224A include threads/ratchets 236, threads/ratchets 236 would resist linear rearward movement (or backing out) of fasteners 220 from apertures 230.

Head portion 202, as depicted in FIG. 5, is generally shaped as a substantially semi-hollow spherical cap. Head portion 202 includes an articular surface 240, an interior surface 241, a bone-contacting rim 242, an interior cavity 243 delineated at least in part by interior surface 241 and bone-contacting rim 242, and columns 244, 246, and 248 extending outwardly from interior surface 241 into interior cavity 243. Articular surface 240 is substantially similar to the shape of the articular surface of the humeral head (or portions thereof) for which it is used in replacing. The thickness of head portion 202 between articular and interior surfaces 240 and 241 can vary. As depicted in FIG. 5, bone-contacting rim 242 is formed at a base 250 of head portion 202, and contacts surface $S_6$ of humerus H. Bone-contacting rim 242 can be configured to accommodate the shape of surface $S_6$, and surface $S_6$ can be prepared to interface with the shape of bone-contacting rim 242.

Columns 244, 246, and 248 include apertures 232 for receiving fasteners 220, and unfractured bone of humerus H, bone fragments of humerus H, and/or a substrate (not shown) can fill interior cavity 243. The unfractured bone of humerus H, the bone fragments of the humerus H, and/or the substrate can be provided between base 250, and interior surface 241 and columns 244, 246, and 248. When interior cavity 243 is filled with the unfractured bone of humerus H, the bone fragments of the humerus H, and/or the substrate, apertures 230 would extend through the unfractured bone of humerus H, the bone fragments of humerus H, and/or the substrate provided therein. As depicted in FIG. 5, the unfractured bone of humerus H fills interior cavity 243. As such, apertures 230 extend through the unfractured bone of humerus H filling interior cavity 243. Furthermore, apertures 230 and 232 abut one another, and surface $S_7$ of humerus H contacts interior surface 241. Surface $S_7$ can be prepared to interface with the shape of interior surface 241, and vice versa.

Columns 244, 246, and 248 can have different orientations with respect to one another to accommodate the desired orientations of fasteners 220. Furthermore, columns 244, 246, and 248 can have different heights with respect to interior surface 241 of head portion 202. As such, columns 244, 246, and 248 can be extended toward base 250, and, provided that there is no interference therebetween, columns 244, 246, and 248 can have markedly different orientations and heights. Columns 244, 246, and 248, as depicted in FIG. 5, are oriented at angles in accordance with the angles of fasteners 220. While the heights of columns 244, 246, and 248 depicted in FIG. 5 have short profiles relative to interior surface 241, columns 244, 246, and 248 can instead have tall profiles relative to interior surface 241.

Depending on whether second portions 224B have regular roughened surfaces, irregular roughened surfaces, and/or smoothened surfaces, engagement of fasteners 220 to head portion 202 would be different. For example, if second portions 224B include threads/ratchets 256, second portions 224B can engage (via complimentary structures formed in and/or via interference, press, and/or friction fits with) apertures 232. Furthermore, if second portions 224B have smoothened surfaces, second portions 224B can engage (via interference, press, and/or friction fits) surfaces formed in apertures 232. The interactions afforded by the complimentary structures and interference, press, and/or friction fits serve in attaching fasteners 220 to head portion 202 by resisting linear movement (or backing out) of fasteners 220 from head portion 202 after insertion into apertures 232.

Fifth humeral head replacement system 260 is depicted in FIG. 6 in position with respect to humerus H. Humeral head replacement system 260 includes a head or prosthetic portion 262 and a bone plate portion 264. Like head portion 22, head portion 262 serves as a prosthesis for replacement of the humeral head or portions thereof, and, like bone plate portion 24, bone plate portion 264 is attached to humerus H to provide a rigid structure for attaching head portion 262 thereto. The rigid structure provided by the attachment of bone plate portion 264 to humerus H allows head portion 262 to be secured in position on humerus H.

As depicted in FIG. 6, bone plate portion 264 is attached to humerus H, and includes a first portion 266 and a second portion 268. First portion 266 is used in attaching bone plate portion 264 to humerus H at or adjacent surgical neck SN, and second portion 268 is used in attaching bone plate portion 264 to at least one of greater or lesser tubercles T. Bone plate portion 264 includes a length and a longitudinal axis extending between a first end 270 and a second end 272. Furthermore, like the width of bone plate portion 24, the width (i.e., the dimensions perpendicular to the length) of bone plate portion 264 can vary along the length thereof to facilitate contact with different portions of humerus H. For example, second portion 268 can be wider than first portion 266 to accommodate contact thereof with both of greater and lesser tubercles T. An illustrative shape for the perimeter of bone plate portion 264 can be seen in FIG. 7.

Like bone plate portion 24, bone plate portion 264 includes both an upper surface 274 and a lower surface 276 extending along first and second portions 266 and 268. Like lower surface 36 of first and second portions 26 and 28, lower surface 276 of first and second portions 266 and 268 can be contoured to contact different portions of humerus H.

Furthermore, although not depicted in FIG. 6, first portion 266 can include apertures (similar to apertures 42) extending between upper and lower surfaces 274 and 276 that are configured for receiving fasteners such as bone screws 40. Like first portion 26 of bone plate portion 24, first portion 266 of bone plate portion 264 can be attached at or adjacent surgical neck SN using bone screws 40. Bone screws 40 can engage the apertures formed in first portion 266, as well as apertures (not shown) formed in humerus H.

Second portion 268 of bone plate portion 264 is configured to receive one or more fasteners 280 therethrough to facilitate attachment of head portion 262, bone plate portion 264, and humerus H to one another. To that end, second portion 268 can include one or more apertures 282 therethrough (extending between upper and lower surfaces 274 and 276) for receiving fasteners 280. Fasteners 280 can each include a shaft 284 and a head 286. Shafts 284 can serve in facilitating engagement with head portion 262 and humerus H, and heads 286 can serve in facilitating engagement with second portion 268. When lower surface 276 (at second portion 268) is properly positioned with respect to humerus H, fasteners 280 can be inserted into apertures 282, into apertures 290 formed in humerus H, and into apertures 292 formed in head portion 262. Furthermore, apertures 282 can be countersunk to receive heads 286, so that at least portions of heads 286 ultimately can lie below upper surface 274.

Three fasteners 280 and three apertures 282 are depicted in FIG. 6 arranged to have a generally parallel orientation with respect to one another. Fasteners 280 and apertures 282 are spaced along the longitudinal axis of bone plate portion 264. Furthermore, in similar fashion to apertures 52 (and corresponding fasteners 50) of first humeral head replacement system 20, the number, arrangement, spacing, and orientation of apertures 282 (and hence, corresponding fasteners 280) can vary further. Like with first humeral head replacement system 20, these variations (such as the positioning thereof on either side of the longitudinal axis and pattern formed thereby) for apertures 282 (and corresponding fasteners 280) can occur because second portion 268 is sized to contact varying portions of humerus H, and the desire to have the fasteners 280 parallelly or obliquely oriented with respect to one another.

Like shafts 54 and heads 56, shafts 284 and heads 286 can be configured to have cylindrical or frusto-conical shaped portions, and have regular roughened surfaces, irregular roughened surfaces, and/or smoothened surfaces provided on the cylindrical or frusto-conical shaped portions. Furthermore, like shafts 54, shafts 284 can include first portions 284A used in engaging apertures 290 formed through humerus H, and second portions 284B used in engaging corresponding surfaces of apertures 292 formed in head portion 262. First and second portions 284A and 284B can be configured to have identical or different shapes, lengths, and widths, and can include the above-discussed regular roughened surfaces, irregular roughened surfaces, and/or smoothened surfaces.

The connection between head portion 262 and bone plate portion 264 afforded by fasteners 280 serves in maintaining the positions of the components of humeral head replacement system 260 relative to humerus H. Indeed, portions of humerus H are clamped between head portion 262 and bone plate portion 264. Furthermore, in addition to the connection between head portion 262 and bone plate portion 264 afforded thereby, the configuration of fasteners 280 can serve in resisting movement (and hence, maintaining the position) of the components of humeral head replacement system 260 relative to humerus H. That is, the regular or irregular roughened surfaces formed on shafts 284 can serve in fixing fasteners 280 relative to humerus H. For example, if first portions 284A include threads/ratchets 296, threads/ratchets 296 would resist linear rearward movement (or backing out) of fasteners 280 from apertures 290.

Head portion 262, as depicted in FIG. 6, is generally shaped as a substantially semi-hollow spherical cap. Head portion 262 includes an articular surface 300, an interior surface 301, a bone-contacting rim 302, an interior cavity 303 delineated at least in part by interior surface 301 and bone-contacting rim 302, and columns 304, 306, and 308 extending outwardly from interior surface 301 into interior cavity 303. Articular surface 300 is substantially similar to the shape of the articular surface of the humeral head (or portions thereof) for which it is used in replacing. The thickness of head portion 262 between articular and interior surfaces 300 and 301 can vary. As depicted in FIG. 6, bone-contacting rim 302 is formed at a base 310 of head portion 262, and contacts surface $S_8$ of humerus H. Bone-contacting rim 302 can be configured to accommodate the shape of surface $S_8$, and surface $S_8$ can be prepared to interface with the shape of bone-contacting rim 302.

Columns 304, 306, and 308 include apertures 292 for receiving fasteners 280. Like columns 244, 246, and 248, columns 304, 306, and 308 can have different orientations with respect to one another, and can have different heights with respect to interior surface 301 of head portion 262. Columns 304, 306, and 308, as depicted in FIG. 6, extend from interior surface 301 to terminate adjacent base 310. As such, surfaces 314, 316, and 318 of columns 304, 306, and 308, respectively, contact surface $S_9$ of humerus H. Furthermore, columns 304, 306, and 308 depicted in FIG. 6 have generally parallel orientations with respect to one another, and have different heights relative to interior surface 301. Although not depicted in FIG. 6, unfractured bone of humerus H, bone fragments of humerus H, and/or a substrate can be provided in interior cavity 303 around columns 304, 306, 308, and can extend from base 310 to interior surface 301.

Depending on whether second portions 284B have regular roughed surfaces, irregular roughened surfaces, and/or smoothened surfaces, engagement of fasteners 280 to head portion 262 would be different. The configuration of apertures 292 formed in columns 304, 306, and 308 would be configured to accommodate the regular roughened surfaces, irregular roughened surfaces, and/or smoothened surfaces formed on second portions 284B. For example, apertures 292 of head portion 262 depicted in FIG. 6 have threads/ratchets 320 to engage threaded/ratchets 326 formed on second portions 284B; and apertures 292 of head portion 262A depicted in FIG. 6A have smoothened surfaces 322 to engage smoothened surfaces 328 formed on second portions 284B. The interactions afforded by the complimentary structures and interference, press, and/or friction fits serve in attaching fasteners 280 to head portions 262 and 262A by resisting linear movement (or backing out) of fasteners 280 from head portion 262 after insertion into apertures 292.

As depicted in FIGS. 6 and 6A, for example, apertures 292 and corresponding fasteners 280 are sized similarly. However, one of more differently sized fasteners can be used for attaching a head portion, a bone plate portion, and humerus H in the humeral head replacement systems described herein.

Sixth humeral head replacement system 340 depicted in FIG. 7 uses such differently sized fasteners. Humeral head replacement system 340 includes a head or prosthetic portion 342 and a bone plate portion 344. Head portion 342 and bone plate portion 344 function similarly to and can include the features of head portion 262 and bone plate portion 264 of humeral head replacement system 260. However, rather than including similarly sized fasteners for attaching head portion 342, bone plate portion 344, and humerus H to one another, humeral head replacement system 340 includes at least one oversized fastener 350 to facilitate such attachment. Oversized fastener 350 and additional fasteners (not shown) of humeral head replacement system 340 can function similarly to and include the features of fasteners 280 of humeral head replacement system 260.

Bone plate portion 344 includes an aperture 352 for receiving oversized fastener 350, and apertures 354 for receiving the additional fasteners having smaller diameters than oversized fastener 350. As depicted in FIG. 7, apertures 354 have a diamond-shaped pattern surrounding aperture 352. However, like apertures 282, the number, arrangement, spacing, and orientation of apertures 352 and 354 can vary. Head portion 342 includes apertures 356 and 358 corresponding to apertures 352 and 354, respectively. That is, aperture 356 can receive oversized fastener 350, and apertures 358 can receive the additional fasteners. Apertures 356 and 358, as depicted in FIG. 7, are formed in columns 360 and 362, respectively.

Depending on the configurations of oversized fastener 350 and additional fasteners, engagement with humerus and apertures 356 and 358, respectively, would be different. Like fasteners 280, fastener 305 and additional fasteners could include regular roughened surfaces, irregular roughened surfaces, and smoothened surfaces to engage humerus H, and engage complimentary structures and/or engage (via interference, press, and/or friction fits) surfaces formed in apertures 356 and 358.

Seventh humeral head replacement system 380 is depicted in FIG. 8 in position with respect to humerus H. Humeral head replacement system 380 includes a head or prosthetic portion 382 and a bone plate portion 384. Like head portion 22, head portion 382 serves as a prosthesis for replacement of the humeral head or portions thereof, and, like bone plate portion 24, bone plate portion 384 is attached to humerus H to provide a rigid structure for attaching head portion 382 thereto. The rigid structure provided by the attachment of bone plate portion 384 to humerus H allows head portion 382 to be secured in position on humerus H.

As depicted in FIG. 8, bone plate portion 384 is attached to humerus H, and includes a first portion 386 and a second portion 388. First portion 386 is used in attaching bone plate portion 384 to humerus H at or adjacent surgical neck SN, and second portion 388 is used in attaching bone plate portion 384 to at least one of greater or lesser tubercles T. Bone plate portion 384 includes a length and a longitudinal axis extending between a first end 390 and a second end 392. Furthermore, like the width of bone plate portion 24, the width (i.e., the dimensions perpendicular to the length) of bone plate portion 384 can vary along the length thereof to facilitate contact with different portions of humerus H. For example, second portion 388 can be wider than first portion 386 to accommodate contact thereof with both of greater and lesser tubercles T. An illustrative shape for the perimeter of bone plate portion 384 can be seen in FIG. 7.

Like bone plate portion 24, bone plate portion 384 includes both an upper surface 394 and a lower surface 396 extending along first and second portions 386 and 388. Like lower surface 36 of first and second portions 26 and 28, lower surface 396 of first and second portions 386 and 388 can be contoured to contact different portions of humerus H.

Furthermore, although not depicted in FIG. 8, first portion 386 can include apertures (similar to apertures 42) extending between upper and lower surfaces 394 and 396 that are configured for receiving fasteners such as bone screws 40. Like first portion 26 of bone plate portion 24, first portion 386 of bone plate portion 384 can be attached at or adjacent surgical neck SN using bone screws 40. Bone screws 40 can engage the apertures formed in first portion 386, as well as apertures (not shown) formed in humerus H.

In addition to first portion 386 being attached at or adjacent surgical neck SN using fasteners such as bone screws 40, second portion 388 can be configured to receive one or more of fasteners such as bone screws 40 therethrough to attach second portion 388 above surgical neck SN. As depicted in FIG. 8, second portion 388 includes apertures 400 extending between upper and lower surfaces 394 and 396 for receiving bone screws 40, and humerus H includes apertures 402 for receiving bone screws 40. Threaded shafts 44 (of bone screws 40) can serve in facilitating engagement with apertures 402 formed in humerus H, and threaded heads 46 (of bone screws 40) can serve in facilitating engagement with second plate portion 388 via complimentary threads (not shown) provided in apertures 400. When lower surface 396 (at first portion 386) is properly positioned with respect to humerus H, bone screws 40 can be inserted into apertures 400 and into humerus H to further secure bone plate portion 384 to humerus H. Furthermore, apertures 400 can be countersunk to receive threaded heads 46, so that at least portions of threaded heads 46 ultimately can lie below upper surface 394.

Rather than or in addition to using fasteners (such as fasteners 50 of humeral head replacement system 20), bone plate portion 384 can include one or more integrally formed posts for insertion into a portion of head portion 382. As depicted in FIG. 8, bone plate portion 384 includes a post 404 extending outwardly from lower surface 396 (at second portion 388). Post 404 can be used to facilitate attachment of head portion 382, bone plate portion 384, and humerus H to one another.

Post 404 includes a first shaft portion 406 and a second shaft portion 408. First shaft portion 406 can serve in facilitating engagement with an aperture 410 formed in humerus H, and second shaft portion 408 can serve in facilitating engagement with an aperture 412 formed in head portion 382. In essence, second shaft portion 408 of post 404 serves as a male component to be received in a female component afforded by aperture 412 formed in head portion 382. During positioning of head portion 382 and bone plate portion 384 with respect to humerus H, post 404 can be inserted into aperture 410 formed in humerus H, and into aperture 412 formed in head portion 382. As discussed below, post 404 and aperture 412 can include regular roughened surfaces, irregular roughened surfaces, and/or smoothened surfaces to facilitate a connection therebetween.

As discussed above, one or more posts 404 can be formed on bone plate portion 384. For example, multiple posts 404 can be spaced along the longitudinal axis of bone plate portion 384. Furthermore, in similar fashion to apertures 52 (and corresponding fasteners 50) of first humeral head replacement system 20, the number, arrangement, and spacing of multiple posts 404 can vary further. Like with apertures 52 (and corresponding fasteners 50) of first humeral head replacement system 20, these variations (such as the positioning thereof on either side of the longitudinal axis and pattern formed thereby) for multiple posts 404 can occur because second portion 388 is sized to contact varying portions of humerus H. These variations can also occur because the desire to have multiple posts 404 obliquely oriented with respect to head portion 382—multiple posts 404 would likely be parallel or close to parallel to one another to afford engagement with head portion 382.

Like first and second portions 54A and 54B of shafts 54, first and second shaft portions 406 and 408 of post 404 can be configured to have cylindrical or frusto-conical shaped portions, and have regular roughened surfaces, irregular roughened surfaces, and/or smoothened surfaces provided on the cylindrical or frusto-conical shaped portions for engaging corresponding surfaces provided in apertures 410 and 412.

As depicted in FIG. 8, the connection between head portion 382 and bone plate portion 384 afforded by the interaction between the surfaces of post 404 and aperture 412 serves in maintaining the positions of the components of humeral head replacement system 380 relative to humerus H. Indeed, portions of humerus H are clamped between head portion 382 and bone plate portion 384. Furthermore, the configuration of post 404 can serve in resisting movement (and hence, maintaining the position) of the components of humeral head replacement system 380 relative to humerus H. For example, if first shaft portion 406 includes threads/ratchets (not shown), the threads/ratchets would resist linear rearward movement (or backing out) of post 404 from aperture 410, and, in doing so, serve in fixing post 404 relative to humerus H.

As depicted in FIG. 8, head portion 382 is generally shaped as a substantially semi-hollow spherical cap. Head portion 382, as depicted in FIG. 8, includes an articular surface 416, an interior surface 418, a bone-contacting rim 420, an interior cavity 422, and a column 424. Articular surface 416 is substantially similar to the shape of the articular surface of the humeral head (or portions thereof) for which it is used in replacing. Head portion 382, however, is not limited to the features depicted in FIG. 8. Where compatible, head portion 382 could instead include the features of the other head portions described herein.

As depicted in FIG. 8, interior cavity 422 is provided at least in part between interior surface 418 and bone-contacting rim 420, and column 424 is depicted extending outwardly from interior surface 418 into interior cavity 422. The thickness of head portion 382 between articular and interior surfaces 416 and 418 can vary. As depicted in FIG. 8, bone-contacting rim 420 is formed at a base 426 of head portion 382, and contacts surface $S_{10}$ of humerus H. Bone-contacting rim 420 can be configured to accommodate the shape of surface $S_{10}$, and surface $S_{10}$ can be prepared to interface with the shape of bone-contacting rim 420. Moreover, although not depicted in FIG. 8, unfractured bone of humerus H, bone fragments of humerus H, and/or a substrate can be provided in interior cavity 422 around column 424, and can extend from base 426 to interior surface 418.

As discussed above, column 424 includes aperture 412 for receiving second shaft portion 408 of post 404. Column 424 can have varying orientations to accommodate the orientation of post 404, and can have varying heights with respect to interior surface 418 of head portion 382. Column 424, as depicted in FIG. 8, extends from interior surface 418 to terminate beyond base 426. As such, surface 428 of column 424 contacts surface $S_{11}$ of humerus H. Furthermore, if multiple posts 404 are formed on bone plate portion 384, multiple columns 424 and corresponding apertures 412 can be provided to receive multiple posts 404, and multiple columns 424 can have different heights with respect to interior surface 418 of head portion 382.

Depending on whether second shaft portion 408 of post 404 has regular roughed surfaces, irregular roughened surfaces, and/or smoothened surfaces, engagement of post 404 to head portion 382 would be different. Aperture 412 formed in column 424 would be configured to accommodate the regular roughened surfaces, irregular roughened surfaces, and/or smoothened surfaces formed on second shaft portion 408. For example, if second shaft portion 408 includes threads/ratchets (not shown), second shaft portion 408 can engage (via complimentary structures formed in and/or via interference, press, and/or friction fits with) aperture 412. Furthermore, if second shaft portion 408 has a smoothened surface 430, second shaft portion 408 can engage (via interference, press, and/or friction fits) a smoothened surface 432 formed in aperture 412. The interactions afforded by the complimentary structures and interference, press, and/or friction fits serve in attaching post 404 to head portion 382 by resisting linear movement (or backing out) of post 404 from head portion 382 after insertion into aperture 412.

Eighth humeral head replacement system 440 is depicted in FIG. 9 in position with respect to humerus H. Humeral head replacement system 440 includes a head or prosthetic portion 442 and a bone plate portion 444. Like the head portion 22, head portion 442 serves as a prosthesis for replacement of the humeral head or portions thereof, and, like bone plate portion 24, bone plate portion 444 is attached to humerus H to provide a rigid structure for attaching head portion 442 thereto. The rigid structure provided by the attachment of bone plate portion 444 to the humerus H allows head portion 442 to be secured in position on humerus H.

As depicted in FIG. 9, bone plate portion 444 is attached to humerus H, and includes a first portion 446 and a second portion 448, and includes both an upper surface 450 and a lower surface 452 extending along first and second portions 446 and 448. Bone plate portion 444 can include many of the features of above-discussed bone plate portion 384. As such, first portion 446 can be attached at or adjacent surgical neck SN in similar fashion to first portion 386 of bone plate portion 384, and second portion 448 can be attached to at least one of greater or lesser tubercles T above surgical neck SN.

However, instead of post 404, bone plate portion 444 includes one or more integrally formed posts for receiving a portion of head portion 442. As depicted in FIG. 9, bone plate portion 444 includes a post 454 extending outwardly from lower surface 452 (at second portion 448). Post 454 can be used to facilitate attachment of head portion 442, bone plate portion 444, and humerus H to one another.

Post 454 includes a first shaft portion 456 and a second shaft portion 458. First and second shaft portions 456 and 458 can include the features of first and second shaft portions 406 and 408 of post 404. As such, first and second shaft portions 456 and 458 can be configured to have cylindrical or frusto-conical shaped portions, and have regular roughened surfaces, irregular roughened surfaces, and/or smoothened surfaces provided on the cylindrical or frusto-conical shaped portions.

First shaft portion 456 can serve in facilitating engagement with an aperture 460 formed in humerus H, and second shaft portion 458 includes a depression (or aperture) 462 serving to facilitate engagement with a column 464 formed on head portion 442. In essence, depression 462 formed in post 454 serves as a female component for receipt of a male component afforded by column 464 formed on head portion 442. During positioning of head portion 442 and bone plate portion 444 with respect to humerus H, post 454 can be inserted into aperture 460 formed in humerus H. Thereafter, column 464 of head portion 442 can be inserted into depression 462 formed in post 454. As discussed below, depression 462 and column 464 can include regular roughened surfaces, irregular roughened surfaces, and/or smoothened surfaces to facilitate a connection therebetween. Furthermore, to further secure the connection therebetween, post 454 and column 464 can include apertures 470 and 472, respectively, for receiving a fastener 474. Aperture 470 extends into post 454 from depression 462, and aperture 472 extends through column 464.

As discussed above, one or more posts 454 can be formed on bone plate portion 444. For example, multiple posts 454 can be spaced along longitudinal axis of bone plate portion 444. Furthermore, in similar fashion to apertures 52 (and corresponding fasteners 50) of first humeral head replacement system 20, the number, arrangement, and spacing of multiple posts 454 can vary further. Like with apertures 52 (and corresponding fasteners 50) of first humeral head replacement system 20, these variations (such as the positioning thereof on either side of the longitudinal axis and pattern formed thereby) for multiple posts 454 can occur because second portion 448 is sized to contact varying portions of humerus H. These variations can also occur because of the desire to have multiple posts 454 obliquely oriented with respect to head portion 442—multiple posts 454 would likely be parallel or close to parallel to one another to afford engagement with head portion 442.

As depicted in FIG. 9, the connection between head portion 442 and bone plate portion 444 afforded by the interaction between the surfaces of depression 462 and column 464 serves in maintaining the positions of the components of humeral head replacement system 440 relative to humerus H. Indeed, portions of humerus H are clamped between head portion 442 and bone plate portion 444. Furthermore, the configuration of post 454 can serve in resisting movement (and hence, maintaining the position) of the components of humeral head replacement system 440 relative to humerus H. For example, if first shaft portion 456 includes threads/ratchets (not shown), the threads/ratchets would resist linear rearward movement (or backing out) of post 454 from aperture 460, and, in doing so, serve in fixing post 454 relative to humerus H.

As depicted in FIG. 9, head portion 442 is generally shaped as a substantially semi-hollow spherical cap. Head portion 442, as depicted in FIG. 9, includes an articular surface 476, an interior surface 478, a bone-contacting rim 480, an interior cavity 482, column 464, and aperture 472 formed through column 464. Articular surface 476 is substantially similar to the shape of the articular surface of the humeral head (or portions thereof) for which it is used in replacing. Furthermore, head portion 442 can include an aperture 484 formed in articular surface 476 and interconnected with aperture 472. Head portion 442, however, is not limited to the features depicted in FIG. 9. Where compatible, head portion 442 could instead include the features of the other head portions described herein.

As depicted in FIG. 9, interior cavity 482 is provided in least in part between interior surface 478 and bone-contacting rim 480, and column 464 is depicted extending outwardly from interior surface 478 into interior cavity 482. The thickness of head portion 442 between articular and interior surfaces 476 and 478 can vary. As depicted in FIG. 9, bone-contacting rim 480 is formed at a base 486 of head portion 442, and contacts surface $S_{12}$ of humerus H. Bone-contacting rim 480 can be configured to accommodate the shape of surface $S_{12}$, and surface $S_{12}$ can be prepared to interface with the shape of bone-contacting rim 480. Moreover, although not depicted in FIG. 9, unfractured bone of humerus H, bone fragments of humerus H, and/or a substrate can be provided in interior cavity 482 around column 464, and can extend from base 486 to interior surface 478.

As discussed above, column 464 is received in depression 462 formed in post 454. Column 464 can have varying orientations to accommodate the orientation of post 454, and can have varying heights with respect to interior surface 478 of head portion 442. Column 464, as depicted in FIG. 9, extends from interior surface 478 to terminate beyond base 486. Furthermore, if multiple posts 454 are formed on bone plate portion 444, multiple columns 464 can be provided to be received in corresponding multiple depressions 462 of multiple posts 454, and multiple columns 464 can have different heights with respect to interior surface 478 of head portion 442.

Depending on whether depression 462 of post 454 has regular roughed surfaces, irregular roughened surfaces, and/or smoothened surfaces, engagement of head portion 442 to post 454 would be different. Column 464 would be correspondingly configured to accommodate the regular roughened surfaces, irregular roughened surfaces, and/or smoothened surfaces formed in depression 462. For example, if depression 462 includes threads/ratchets (not shown), depression 462 can (engage via complimentary structures formed on and/or via interference, press, and/or friction fits with) column 464. Furthermore, if depression 462 has a smoothened surface 490, depression 462 can engage (via interference, press, and/or friction fits) a smoothened surface 492 formed on column 464. The interactions afforded by the complimentary structures and interference, press, and/or friction fits serve in attaching head portion 442 to post 454 of bone plate portion 444 by resisting linear movement (or backing out) of column 464 of head portion 442 from depression 462 of post 454.

As discussed above, fastener 474 can be used to further secure head portion 442 and bone plate portion 444 to one another. As depicted in FIG. 9, when column 464 is received in depression 462 of post 454, aperture 470 formed in post 454, aperture 472 formed in column 464, and aperture 484 formed in articular surface 476 are aligned with one another. Such alignment allows fastener 474 to be inserted through aperture 484 and into apertures 470 and 472. A shoulder 494 can be provided in aperture 472 formed in column 464 to contact fastener 474 to prevent further insertion. Furthermore, fastener 474 can include regular roughened surfaces, irregular roughened surfaces, and/or smoothened surfaces 496 to interact with a corresponding surfaces 498 provided in aperture 470 to further secure head portion 442 and bone plate portion 444.

Ninth humeral head replacement system 510 is depicted in FIG. 10 in position with respect to humerus H. Humeral head replacement system 510 includes a head or prosthetic portion 512, a bone plate portion 514, and an intermediate portion 515. Like head portion 22, head portion 512 serves as a prosthesis for replacement of the humeral head or portions thereof, and, like bone plate portion 24, bone plate portion 514 is attached to humerus H to provide a rigid structure for attaching intermediate portion 515 thereto. Intermediate portion 515 can be provided within humerus H and attached to bone plate portion 514 to provide a rigid structure for attaching head portion 512 thereto. The rigid structure provided by bone plate portion 514 and intermediate portion 515 allows head portion 512 to be secured in position on humerus H.

As depicted in FIG. 10, bone plate portion 514 is attached to humerus H, and includes a first portion 516 and a second portion 518. First portion 516 is used in attaching bone plate portion 514 to humerus H at or adjacent surgical neck SN, and second portion 518 is used in attaching bone plate portion 514 to at least one of greater or lesser tubercles T. Bone plate portion 514 includes a length and a longitudinal axis extending between a first end 520 and a second end 522. Furthermore, like the width of bone plate portion 24, the width (i.e., the dimensions perpendicular to the length) of bone plate portion 514 can vary along the length thereof to facilitate contact with different portions of humerus H. For example, second portion 518 can be wider than first portion 516 to accommodate contact thereof with both of greater and lesser tubercles T. An illustrative shape for the perimeter of bone plate portion 514 can be seen in FIG. 7.

Like bone plate portion 24, bone plate portion 514 includes both an upper surface 524 and a lower surface 526 extending along first and second portions 516 and 518. Like lower surface 36 of first and second portions 26 and 28, lower surface 526 of first and second portions 516 and 518 can be contoured to contact different portions of humerus H.

Furthermore, although not depicted in FIG. 10, first portion 516 can include apertures (similar to apertures 42) extending between upper and lower surfaces 524 and 526 that are configured for receiving fasteners such as bone screws 40. Like first portion 26 of bone plate portion 24, first portion 516 of bone plate portion 514 can be attached at or adjacent surgical neck SN using bone screws 40. Bone screws 40 can engage the apertures formed in first portion 516, as well as apertures (not shown) formed in humerus H.

Second portion 518 of bone plate portion 514 is configured to receive one or more fasteners 530 therethrough. Fasteners 530 are used to facilitate attachment of intermediate portion 515 and bone plate portion 514 to one another. In addition, fasteners 530 can engage humerus H, and can also be used to secure humerus H between bone plate portion 514 and intermediate portion 515. To those ends, second portion 518 can include one or more apertures 532 therethrough (extending between upper and lower surfaces 524 and 526) for receiving fasteners 530.

Fasteners 530 can each include a shaft 534 and a head 536. Shafts 534 can serve in facilitating engagement with intermediate portion 515 and humerus H, and heads 536 can serve in facilitating engagement with apertures 532 of second portion 518. When lower surface 526 (at second portion 518) is properly positioned with respect to humerus H, fasteners 530 can be inserted into apertures 532, into apertures 540 formed in humerus H, and into apertures 542 formed in intermediate portion 515. Furthermore, apertures 532 can be countersunk to receive heads 536, so that at least portions of heads 536 ultimately can lie below upper surface 524.

Three fasteners 530 and three apertures 532 are depicted in FIG. 10 arranged to have a generally parallel orientation with respect to one another. Fasteners 530 and apertures 532 are spaced along the longitudinal axis of bone plate portion 514. Furthermore, in similar fashion to apertures 52 (and corresponding fasteners 50) of first humeral head replacement system 20, the number, arrangement, spacing, and orientation of apertures 532 (and hence, corresponding fasteners 530) can vary further. Like with first humeral head replacement system 20, these variations (such as the positioning thereof on either side of the longitudinal axis and pattern formed thereby) for apertures 532 (and corresponding fasteners 530) can occur because second portion 518 is sized to contact varying portions of humerus H, and the desire to have the fasteners 530 parallelly or obliquely oriented with respect to one another.

Like shafts 54 and heads 56, shafts 534 and heads 536 can be configured to have cylindrical or frusto-conical shaped portions, and have regular roughened surfaces, irregular roughened surfaces, and/or smoothened surfaces provided on the cylindrical or frusto-conical shaped portions. Furthermore, apertures 532 can include corresponding surfaces to facilitate engagement with heads 536, and apertures 540 and 542 can include corresponding surfaces to facilitate engagement with shafts 534. As such, fasteners 530 can interact with apertures 532, 540, and 542 to attach bone plate portion 514, intermediate portion 515, and humerus H together.

Intermediate portion 515 includes a flange (or plate) portion 550 and a post 552 extending outwardly from flange portion 550. Flange portion 550 can be frusto-conical, and includes a first surface 556, second surface 558, and an edge surface 560 extending between first surface 556 and second surface 558. Apertures 542 are formed through first surface 556 and extend into flange portion 550. The number, arrangement, spacing, and orientation of apertures 542 can correspond to the same of apertures 532 formed in bone plate portion 514. Given that flange portion 550 is frusto-conical, the thickness thereof increases from edge surface 560 toward the center of flange portion 550.

Post 552 can be integrally formed with flange portion 550. Furthermore, post 552 can include a first shaft portion 564 and a second shaft portion 566. As depicted in FIG. 10, axes of first and second shaft portions 564 and 566 are aligned with one another. However, as depicted in FIG. 10A, axes of first and second shaft portions 564 and 566 can be acutely oriented with respect to one another.

The flange portion 550 can be other shapes and have other thicknesses. As depicted in FIG. 11, for example, intermediate portion 515A includes a post 552A similar to post 552 depicted in FIG. 10, but also includes a flange portion 550A that has a cylindrical shape with apertures 542A (for receiving fasteners 530) formed therethrough. Flange portion 550A includes a constant thickness between first surface 556A and second surface 558A. Furthermore, as depicted in FIG. 12, for example, intermediate portion 515B includes a post 552B similar to post 552 depicted in FIG. 10, but also includes flange portion 550B that has a tri-lobed shape with apertures 542B (for receiving fasteners 530) formed therethrough. Flange portion 550B includes a constant thickness between first surface 556B and second surface 558B.

As depicted in FIGS. 11 and 12, transitional portions 568A and 568B can be respectively positioned between first and second shaft portions 564A and 565A and first and second shaft portions 564A and 564B. A transitional portion (not shown) can also be positioned between first and second shaft portions 564 and 566 depicted in FIGS. 10 and 10A.

The first shaft portion 564 can serve in facilitating engagement with an aperture 570 formed in humerus H, and second shaft portion 566 can serve in facilitating engagement with an aperture 572 formed in head portion 512. In essence, second shaft portion 566 of post 552 serves as a male component for receipt in a female component afforded by aperture 572 for joining head portion 512 and intermediate portion 515. Like first and second shaft portions 406 and 408 of post 404, first and second shaft portions of 564 and 566 of post 552 can be configured to have cylindrical or frusto-conical shaped portions, and have regular roughened surfaces, irregular roughened surfaces, and/or smoothened surfaces provided on the cylindrical or frusto-conical shaped portions for engaging corresponding surfaces provided in apertures 570 and 572.

As depicted in FIG. 10, the connection between head portion 512 and intermediate portion 515 afforded by the interaction between the surfaces of post 552 and aperture 572 serves in maintaining the positions of head portion 512 and intermediate portion 515 relative to humerus H. Indeed, portions of humerus H are clamped between head portion 512 and intermediate portion 515. Furthermore, the configuration of post 552 can serve in resisting movement (and hence, maintaining the position) of the components of humeral head replacement system 510 relative to humerus H. For example, if first shaft portion 564 includes threads/ratchets (not shown), the threads/ratchets would resist linear rearward movement (or backing out) of post 552 from aperture 570, and, in doing so, serve in fixing post 552 relative to humerus H.

As depicted in FIG. 10, head portion 512 is substantially shaped as a substantially solid spherical cap. Head portion 512 includes an articular surface 576 and a bone-contacting surface 578. Articular surface 576 is substantially similar to the shape of the articular surface (or portions thereof) of the humeral head for which it is used in replacing. Head portion 512, however, is not limited to the features depicted in FIG. 10. Where compatible, head portion 512 could instead include the features of the other head portions described herein. Furthermore, bone-contacting surface 578 contacts humerus H along surface $S_{13}$, and aperture 572 (for receiving second shaft portion 566) extends through bone-contacting surface 578 into head portion 512. As depicted in FIG. 10, bone-contacting surface 578 is substantially flat. However, bone-contacting surface 578 can be concave, convex, or undulating with various concavities and convexities to accommodate the shape of surface $S_{13}$. Surface $S_{13}$ can be prepared to interface with the shape of bone-contacting surface 578.

Depending on whether second shaft portion 566 of post 552 has regular roughed surfaces, irregular roughened surfaces, and/or smoothened surfaces, engagement of post 552 to head portion 512 would be different. Aperture 572 formed in head portion 512 would be configured to accommodate the regular roughened surfaces, irregular roughened surfaces, and/or smoothened surfaces formed on second shaft portion 566. For example, if second shaft portion 566 includes threads/ratchets (not shown), second shaft portion 566 can engage (via complimentary structures formed in and/or via interference, press, and/or friction fits with) aperture 572. Furthermore, if second shaft portion 566 has a smoothened surface 580, second shaft portion 566 can engage (via interference, press, and/or friction fits) a smoothened surface 582 formed in aperture 572. The interactions afforded by the complimentary structures and interference, press, and/or friction fits serve in attaching post 552 to head portion 512 by resisting linear movement (or backing out) of post 552 from head portion 512 after insertion into aperture 572.

Multiple posts 552 can be formed on intermediate portion 515 for engaging multiple apertures 572 formed in head portion 512. For example, in similar fashion to apertures 52 (and corresponding fasteners 50) of first humeral head replacement system 20, the number, arrangement, and spacing of multiple posts 552 and multiple apertures 572 can vary. Like with apertures 52 (and corresponding fasteners 50) of first humeral head replacement system 20, these variations (such as the positioning thereof on either side of the longitudinal axis and pattern formed thereby) for multiple posts 552 can occur because second portion 518 is sized to contact varying portions of humerus H. These variations can also occur because the desire to have multiple posts 552 obliquely oriented with respect to head portion 512—multiple posts 552 would likely be parallel or close to parallel to one another to afford engagement with head portion 512.

In addition, rather than providing second shaft portion 566 of post 552 as the male component, and providing aperture 572 in head portion 512 as the female component for joining head portion 512 and intermediate portion 515, the male and female components could be provided on different components. For example, as depicted in FIG. 13, a projection 586 could be provided on a modified head portion 512M, and an aperture 588 could be provided in a modified post 552M of a modified intermediate portion 515M. Projection 586 serves as a male component for receipt in a female component afforded by aperture 588 for joining head portion 512M and intermediate portion 515M. Projection 586 and aperture 588 could include corresponding regular roughened surfaces, irregular roughened surfaces, and/or smoothened surfaces to facilitate a connection therebetween. Furthermore, like multiple posts 552 and multiple apertures 572 discussed above, multiple projections 586 and multiple apertures 588 can be provided in a similar fashion.

Figure 14:
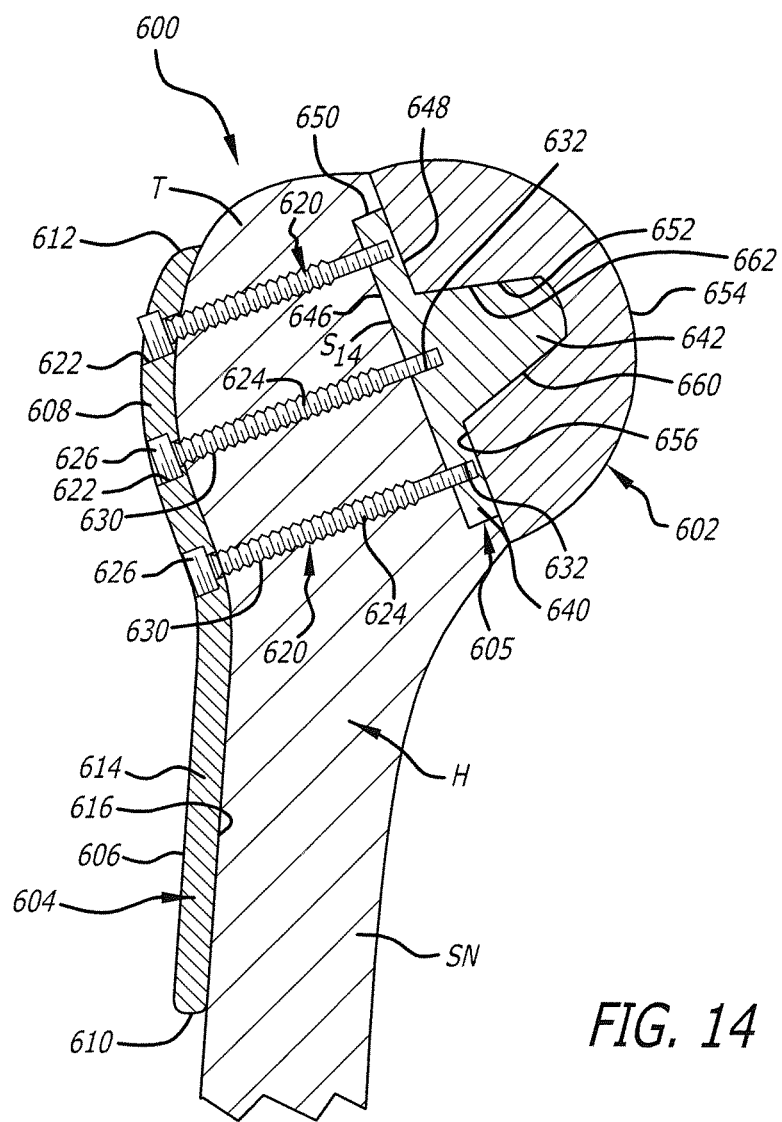
FIG. 14 depicts a partial cross-sectional elevational view of a tenth illustrative embodiment of the humeral head replacement system including a head portion, a bone plate portion, and a base plate portion, the bone plate portion and the base plate portion being attached to one another and a humerus using fasteners, and the base plate portion being attached to the head portion using a post formed integrally with the base plate portion.
Figure 15:
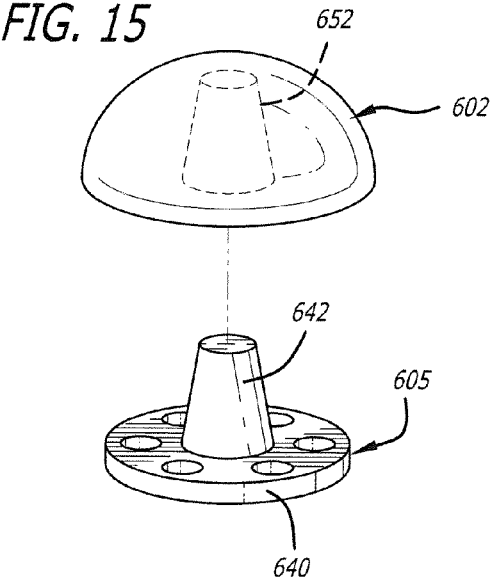
FIG. 15 depicts a perspective exploded-parts view the head portion and the base plate portion depicted in FIG. 14.

The tenth humeral head replacement system 600 is depicted in FIG. 14 in position with respect to humerus H. Humeral head replacement system 600 includes a head or prosthetic portion 602, a bone plate portion 604, and a base plate portion 605. Head portion 602 and base plate portion 605 are also depicted in FIG. 15. Like head portion 22, head portion 602 serves as a prosthesis for replacement of humeral head or portions thereof, and, like bone plate portion 24, bone plate portion 604 is attached to humerus H to provide a rigid structure for attaching base plate portion 605 thereto. Base plate portion 605 can be provided to contact humerus H and attached to bone plate portion 604 to provide a rigid structure for attaching head portion 602 thereto. The rigid structure provided by bone plate portion 604 and base plate portion 605 allows head portion 602 to be secured in position on humerus H.

As depicted in FIG. 14, bone plate portion 604 is attached to humerus H, and includes a first portion 606 and a second portion 608. First portion 606 is used in attaching bone plate portion 604 to humerus H at or adjacent surgical neck SN, and second portion 608 is used in attaching bone plate portion 604 to at least one of greater or lesser tubercles T. Bone plate portion 604 includes a length and a longitudinal axis extending between a first end 610 and a second end 612. Furthermore, like the width of bone plate portion 24, the width (i.e., the dimensions perpendicular to the length) of bone plate portion 604 can vary along the length thereof to facilitate contact with different portions of humerus H. For example, second portion 608 can be wider than first portion 606 to accommodate contact thereof with both of greater and lesser tubercles T. An illustrative shape for the perimeter of bone plate portion 604 can be seen in FIG. 7.

Like bone plate portion 24, bone plate portion 604 includes both an upper surface 614 and a lower surface 616 extending along first and second portions 606 and 608. Like lower surface 36 of first and second portions 26 and 28, lower surface 616 of first and second portions 606 and 608 can be contoured to contact different portions of humerus H.

Furthermore, although not depicted in FIG. 14, first portion 606 can include apertures (similar to apertures 42) extending between upper and lower surfaces 614 and 616 that are configured for receiving fasteners such as bone screws 40. Like first portion 26 of bone plate portion 24, first portion 606 of bone plate portion 604 can be attached at or adjacent surgical neck SN using bone screws 40. Bone screws 40 can engage the apertures formed in first portion 606, as well as apertures (not shown) formed in humerus H.

Second portion 608 of bone plate portion 604 is configured to receive one or more fasteners 620 therethrough. Fasteners 620 are used to facilitate attachment of base plate portion 605 and bone plate portion 604 to one another. In addition, fasteners 620 can engage humerus H, and can also be used to secure humerus H between bone plate portion 604 and base plate portion 605. To those ends, second portion 608 can include one or more apertures 622 therethrough (extending between upper and lower surfaces 614 and 616) for receiving fasteners 620.

Fasteners 620 can each include a shaft 624 and a head 626. Shafts 624 can serve in facilitating engagement with base plate portion 605 and humerus H, and heads 626 can serve in facilitating engagement with apertures 622 of second portion 608. When lower surface 616 (at second portion 608) is properly positioned with respect to humerus H, fasteners 620 can be inserted into apertures 622, into apertures 630 formed in humerus H, and into apertures 632 formed in base plate portion 605. Furthermore, apertures 622 can be countersunk to receive heads 626, so that at least portions of heads 626 ultimately can lie below upper surface 614.

Three fasteners 620 and three apertures 622 are depicted in FIG. 14 arranged to have a generally parallel orientation with respect to one another. Fasteners 620 and apertures 622 are spaced along the longitudinal axis of bone plate portion 604. Furthermore, in similar fashion to apertures 52 (and corresponding fasteners 50) of first humeral head replacement system 20, the number, arrangement, spacing, and orientation of apertures 622 (and hence, corresponding fasteners 620) can vary further. Like with first humeral head replacement system 20, these variations (such as the positioning thereof on either side of the longitudinal axis and pattern formed thereby) for apertures 622 (and corresponding fasteners 620) can occur because second portion 608 is sized to contact varying portions of humerus H, and the desire to have the fasteners 620 parallelly or acutely oriented with respect to one another.

Like shafts 54 and heads 56, shafts 624 and heads 626 can be configured to have cylindrical or frusto-conical shaped portions, and have regular roughened surfaces, irregular roughened surfaces, and/or smoothened surfaces provided on the cylindrical or frusto-conical shaped portions. Furthermore, apertures 622 can include corresponding surfaces to facilitate engagement with heads 626, and apertures 630 and 632 can include corresponding surfaces to facilitate engagement with shafts 624. As such, fasteners 620 can interact with apertures 622, 630, and 632 to attach bone plate portion 604, base plate portion 605, and humerus H together.

Base plate portion 605 includes a flange (or plate) portion 640 and a post 642 extending outwardly from flange portion 640. As depicted in FIG. 15, flange portion 640 is cylindrical, and includes a first surface 646, second surface 648, and an edge surface 650 extending between first surface 646 and second surface 648. Apertures 632 are formed through first surface 646 and extend into flange portion 640. Furthermore, as depicted in FIG. 14, first surface 646 contacts a surface $S_{14}$ of humerus H. Surface $S_{14}$ can be prepared to interface with the shape of flange portion 640, and vice versa.

The number, arrangement, spacing, and orientation of apertures 632 can correspond to the same of apertures 622 formed in bone plate portion 604. Given that flange portion 640 is cylindrical, the thickness of flange portion 640 between first and second surfaces 646 and 648 is constant. However, flange portion 640 can have different shapes and thicknesses. For example, if flange portion 640 is frusto-conical, the thickness would increase from edge surface 650 toward the center of flange portion 640.

Figure 17:
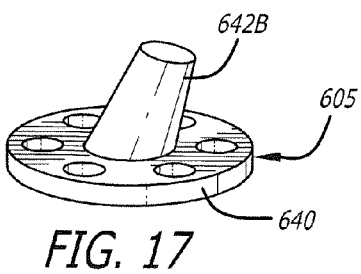
FIG. 17 depicts a perspective view of yet another configuration of a base plate portion for use in the humeral head replacement system of FIG. 14.
Figure 16:
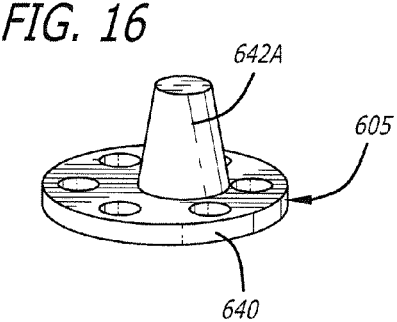
FIG. 16 depicts a perspective view of another configuration of a base plate portion for use in the humeral head replacement system of FIG. 14.

Post 642 can be integrally formed with flange portion 640. As depicted in FIGS. 14 and 15, the axes of flange portion 640 and post 642 are aligned with one another. However, as depicted in FIG. 16, post 642A can be positioned on flange portion 640 such that the axes of flange portion 640 and post 642 are offset from one another, and, as depicted in FIG. 17, axes of post 642B and flange portion 640 can be acutely oriented with respect to one another.

Post 642 can serve in facilitating engagement with an aperture 652 formed in head portion 602. In essence, post 642 serves as a male component for receipt in a female component afforded by aperture 652 for joining head portion 602 and base plate portion 605.

Post 642 can be configured to have cylindrical or frusto-conical shaped portions, and have regular roughened surfaces, irregular roughened surfaces, and/or smoothened surfaces provided on the cylindrical or frusto-conical shaped portions for engaging corresponding surfaces provided in apertures 652. The connection between head portion 602 and base plate portion 605, as depicted in FIG. 14, is afforded by the interaction between the surfaces of post 642 and aperture 652. As discussed below, the interaction serves in maintaining the positions of head portion 602 and base plate portion 605 relative to humerus H.

As depicted in FIGS. 14 and 15, head portion 602 is generally shaped as a substantially solid spherical cap. Head portion 602 includes an articular surface 654 and a flange-contacting surface 656. Articular surface 654 is substantially similar to the shape of articular surface (or portions thereof) of the humeral head for which it is used in replacing. Head portion 602, however, is not limited to the features depicted in FIGS. 14 and 15. Where compatible, head portion 602 could instead include the features of the other head portions described herein. Furthermore, flange-contacting surface 656 contacts flange portion 640 along second surface 648, and aperture 652 (for receiving post 642) extends through flange-contacting surface 656 into head portion 602. As depicted in FIG. 14, flange-contacting surface 656 is substantially flat. However, flange-contacting surface 656 can be shaped to correspond to second surface 648.

Depending on whether post 642 and corresponding aperture 652 have regular roughed surfaces, irregular roughened surfaces, and/or smoothened surfaces, engagement of post 642 to head portion 602 would be different. Aperture 652 formed in head portion 602 would be configured to accommodate the regular roughened surfaces, irregular roughened surfaces, and/or smoothened surfaces formed on post 642. For example, if post 642 includes threads/ratchets (not shown), post 642 can engage (via complimentary structures formed in and/or via interference, press, and/or friction fits with) aperture 652. Furthermore, if post 642 has a smoothened surface 660, post 642 can engage (via interference, press, and/or friction fits) a smoothened surface 662 formed in aperture 652. The interactions afforded by the complimentary structures and interference, press, and/or friction fits serve in attaching post 642 to head portion 602 by resisting linear movement (or backing out) of post 642 from head portion 602 after insertion into aperture 652.

Multiple posts 642 can be formed on base plate portion 605 for engaging multiple apertures 652 formed in head portion 602. For example, in similar fashion to apertures 52 (and corresponding fasteners 50) of first humeral head replacement system 20, the number, arrangement, and spacing of multiple posts 642 and multiple apertures 652 can vary. Like with apertures 52 (and corresponding fasteners 50) of first humeral head replacement system 20, these variations (such as the positioning thereof on either side of the longitudinal axis and pattern formed thereby) for multiple posts 642 can occur because second portion 608 is sized to contact varying portions of humerus H. These variations can also occur because of the desire to have multiple posts 642 obliquely oriented with respect to head portion 602—multiple posts 642 would likely be parallel or close to parallel to one another to afford engagement with head portion 602.

Figure 18:
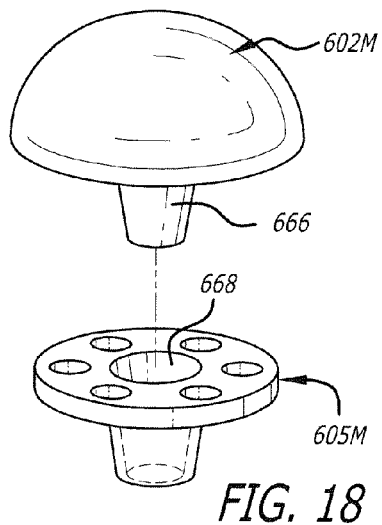
FIG. 18 depicts a perspective exploded-parts view of other configurations of a head portion and a base plate portion for use in the humeral head replacement system of FIG. 14.

In addition, rather than providing post 642 as the male component, and providing aperture 652 in head portion 602 as the female component for joining head portion 602 and base plate portion 605, the male and female components could be provided on different components. For example, as depicted in FIG. 18, a post 666 could be provided on a modified head portion 602M, and an aperture 668 could be provided in a modified base plate portion 605M. Post 666 serves as a male component for receipt in a female component afforded by aperture 668 for joining head portion 602M and base plate portion 605M. Post 666 and aperture 668 could include corresponding regular roughened surfaces, irregular roughened surfaces, and/or smoothened surfaces to facilitate a connection therebetween. Furthermore, like multiple posts 642 and multiple apertures 652 discussed above, multiple posts 666 and multiple apertures 668 can be provided in a similar fashion.

Figure 20:
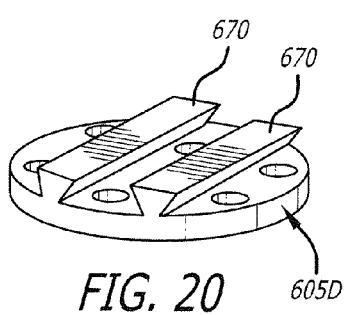
FIG. 20 depicts a perspective view of the base plate portion depicted in FIG. 19.
Figure 19:
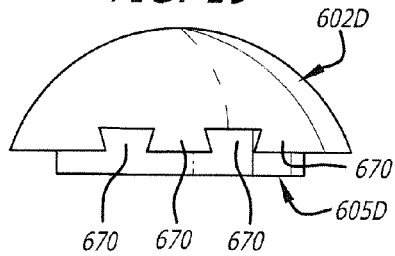
FIG. 19 depicts an elevational view of still other configurations of a head portion and a base plate portion for use in the humeral head replacement system of FIG. 14.

Additionally, rather than providing post 642 and aperture 652 combination or post 666 and aperture 668 combination, head portion 602D and base plate portion 605D, as depicted in FIG. 21, could include dovetail structures 670 formed thereon. Base plate portion 605D is also depicted in FIG. 20. Dovetail structures 670 provide for the connection of head portion 602D and base plate portion 605D to one another.

Distal radius replacement system 700 is depicted in FIGS. 21 and 22 in position with respect to a radius R. Distal radius replacement system 700 includes a prosthetic portion 702 and a bone plate portion 704. Prosthetic portion 702 serves as a prosthesis for replacement of at least a portion of a distal radius. For example, as depicted in FIG. 22, prosthetic portion 702 includes an articular surface 706 which serves in replacing a portion of the carpal articular surface of radius R. Articular surface 706 can facilitate engagement with portions of a wrist including a lunate and a scaphoid.

As depicted in FIG. 22, articular surface 706 is provided between dorsal rim DR and the volar rim VR of the carpal articular surface. However, articular surface 706 also could be used in replacing portions of the dorsal rim DR and the volar rim VR. Furthermore, bone plate portion 704 is attached to radius R to provide a rigid structure for attaching prosthetic portion 702 thereto. The rigid structure provided by the attachment of bone plate portion 704 to radius R allows prosthetic portion 702 to be secured in position on radius R.

As depicted in FIG. 22, bone plate portion 704 is attached to radius R, and, as depicted in FIGS. 21 and 22, bone plate portion 704 includes a first portion 710 and a second portion 712. First portion 710 is used in attaching bone plate portion 704 above the distal end of radius R, and second portion 712 is used in attaching bone plate portion 704 at or adjacent the distal end of radius R. Bone plate portion 704 includes a length and a longitudinal axis extending between a first end 714 and a second end 716. Furthermore, the width (i.e., the dimensions perpendicular to the length) of bone plate portion 704 can vary along the length thereof to facilitate contact with different portions of radius R. For example, as depicted in FIG. 21, second portion 712 is wider than first portion 710 to accommodate contact with the wider portion of radius R at or adjacent the end thereof.

Bone plate portion 704 includes an upper surface 720 and a lower surface 722. Lower surface 722 can be contoured to contact different portions of radius R, and first and second portions 710 and 712 can include apertures 724 and 726, respectively, extending between upper and lower surfaces 720 and 722. First portion 710 of bone plate portion 704 can be attached to radius R using fasteners such as bone screws 40 inserted through apertures 724 and into radius R. Bone screws 40 can engage apertures 724 formed in first portion 710, as well as apertures (not shown) formed in radius R.

Apertures 726 are configured for receiving fasteners 730 (FIG. 22) for attaching prosthetic portion 702, bone plate portion 704, and radius R to one another. While four apertures 726 are depicted in FIG. 21, the number, arrangement, spacing, and orientation of the apertures 726 can vary according to the desired number, arrangement, spacing, and orientation of the fasteners 730.

Fasteners 730 each include a shaft 732 and a head 734. Shafts 732 can serve in facilitating engagement with prosthetic portion 702 and radius R, and heads 734 can serve in facilitating engagement with second portion 712. When lower surface 722 (at second portion 712) is properly positioned with respect to radius R, fasteners 730 can be inserted into apertures 726, into apertures 736 formed in radius R, and into apertures 738 formed in prosthetic portion 702. Furthermore, apertures 726 can be countersunk to receive heads 734, so that at least portions of heads 734 ultimately can lie below upper surface 720.

Like those of fasteners 50, 100, 160, 220, and 280, for example, shafts 732 and heads 734 can be configured to have cylindrical or frusto-conical shaped portions, and have regular roughened surfaces, irregular roughened surfaces, and/or smoothened surfaces provided on the cylindrical or frusto-conical shaped portions. The regular roughened surfaces, irregular roughened surfaces, and/or smoothened surfaces can interface with corresponding surfaces provided in apertures 726, 736, and 738 to afford a connection between prosthetic portion 702, bone plate portion 704, and radius R.

Prosthetic portion 702 includes an articular plate-like portion 740 on which articular surface 706 and a bone-contacting surface 742 is provided, and includes two fastener-receiving protuberances 744 extending outwardly from bone-contacting surface 742. Bone-contacting surface 742 can be prepared to contact surface $S_{15}$. Furthermore, radius R at surface $S_{15}$ can be prepared to engage bone-contacting surface 742, and to accommodate fastener-receiving protuberances 744 therein. Once prosthetic portion 702 and bone plate portion 704 are properly positioned with respect to radius R, fasteners 730 can be used to attach prosthetic portion 702 and bone plate portion 704 to one another, and to radius R.

Fastener-receiving protuberances 744 include apertures 738 for receiving fasteners 730. While two apertures 738 are formed on each of fastener-receiving protuberances 744, the number, arrangement, spacing, and orientation of apertures 738 can vary according to the desired number, arrangement, spacing, and orientation of fasteners 730.

Distal ulna replacement system 800 is depicted in FIG. 23 in position with respect to an ulna U. Distal ulna replacement system 800 includes a prosthetic portion 802 and a bone plate portion 804. Prosthetic portion 802 serves as a prosthesis for replacement of at least a portion of a distal ulna. For example, as depicted in FIG. 23, prosthetic portion 802 includes an articular surface 806 which serves in replacing the articular surface of the head of ulna U. Articular surface 806 can facilitate engagement with portions of the distal radius and portions of a wrist including a lunate.

As depicted in FIG. 23, bone plate portion 804 is attached to ulna U adjacent a styloid process SP to provide a rigid structure for attaching prosthetic portion 802 thereto. The rigid structure provided by the attachment of bone plate portion 802 to ulna U allows prosthetic portion 802 to be secured in position on ulna U.

Bone plate portion 802, as depicted in FIG. 23, includes a first portion 810 and a second portion 812. First portion 810 is used in attaching bone plate portion 804 above the distal end of ulna U, and second portion 812 is used in attaching bone plate portion 804 at or adjacent the distal end of ulna U. Bone plate portion 804 includes a length and a longitudinal axis extending between a first end 814 and a second end 816. Furthermore, the width (i.e., the dimensions perpendicular to the length) of bone plate portion 804 can vary along the length thereof to facilitate contact with different portions of ulna U. For example, as depicted in FIG. 23, second portion 812 is slightly wider than first portion 810.

Bone plate portion 804 includes an upper surface 820 and a lower surface 822. Lower surface 822 can be contoured to contact different portions of ulna U, and first and second portions 810 and 812 can include apertures 824 and 826, respectively, extending between upper and lower surfaces 820 and 822. First portion 810 of bone plate portion 804 can be attached to ulna U using fasteners such as bone screws 40 inserted through apertures 824 and into ulna U. Bone screws 40 can engage apertures 824 formed in first portion 810, as will as apertures (not shown) formed in ulna U.

Apertures 826 are configured for receiving fasteners 830 for attaching prosthetic portion 802, bone plate portion 804, and ulna U to one another. While two apertures 826 are depicted in FIG. 23, the number, arrangement, spacing, and orientation of apertures 826 can vary according to the desired number, arrangement, spacing, and orientation of fasteners 830.

Fasteners 830 each include a shaft 832 and a head 834. Shafts 832 can serve in facilitating engagement with prosthetic portion 802 and ulna U, and heads 834 can service in facilitating engagement with second portion 812. When lower surface 822 (at second portion 812) is properly positioned with respect to ulna U, fasteners 830 can be inserted into apertures 826, into apertures (not shown) formed in ulna U, and into apertures 838 formed in prosthetic portion 802. Furthermore, apertures 826 can be countersunk to receive heads 834, so that at least portions of heads 834 ultimately can lie below upper surface 820.

Like those of fasteners 50, 100, 160, 220, and 280, for example, shafts 832 and heads 834 can be configured to have cylindrical or frusto-conical shaped portions, and have regular roughened surfaces, irregular roughened surfaces, and/or smoothened surfaces provided on the cylindrical or frusto-conical shaped portions. The regular roughened surfaces, irregular roughened surfaces, and/or smoothened surfaces can interface with corresponding surfaces provided in apertures 826 and 838, and apertures formed in ulna U to afford a connection between prosthetic portion 802, bone plate portion 804, and ulna U.

Prosthetic portion 802, as depicted in FIG. 23, is substantially hollow, and includes (in addition to articular surface 806) an interior surface 840, a bone-contacting rim 842, an interior cavity 844, and columns 846. Interior cavity 844 is delineated at least in part by interior surface 840 and bone-contacting rim 842. Articular surface 806 is substantially similar to the shape of the articular surface of the head (or portions thereof) of ulna U for which it is used in replacing. The thickness of prosthetic portion 802 between articular and interior surfaces 806 and 840 can vary, and bone-contacting rim 842 contacts a surface (not shown) of ulna U. The surface of ulna U can be prepared to interface with the shape of bone-contacting rim 842, and vice versa.

Columns 846 include apertures 838 formed therein for receiving fasteners 830, and unfractured bone of ulna U, bone fragments of ulna U, and/or a substrate (not shown) can fill interior cavity 844. While two columns 846 are depicted in FIG. 23, the number, arrangement, spacing, and orientation of columns 846 (and corresponding apertures 838) can vary according to the desired number, arrangement, spacing, and orientation of fasteners 830.

In summary, systems 20, 80, 140, 200, 260, 340, 380, 440, 510, 600, 700, and 800 for replacement of comminuted bone portions and the method for use thereof provide a prosthesis affording replacement of the comminuted bone fractures or portions thereof. Furthermore, while systems 20, 80, 140, 200, 260, 340, 380, 440, 510, 600, 700, and 800 are used in association with the proximal end portion of the humerus, the distal end portion of the radius, or the distal end portion of the ulna, the system and method of the present invention can be configured for use elsewhere in the human body. Other embodiments of the invention will be apparent to those skilled in the art from consideration of the specification and practice of the examples be considered as exemplary only.

I claim:

1. A system for replacement of at least a portion of a comminuted humeral head, the system comprising:
   a prosthesis having an exterior surface and at least one aperture formed therein, said exterior surface being sized and shaped to approximate the surface of the at least a portion of the comminuted humeral head;
   a first plate including a first surface and an opposite second surface, said first surface adapted to contact an exterior portion of a humerus;
   a second plate including a first surface and an opposite second surface, said first surface including at least one post extending outwardly therefrom, and said second surface being adapted to contact an interior portion of the humerus; and
   at least one fastener adapted to attach said first and second plates to one another and the humerus, wherein, when the system is position with respect to the humerus, said first plate and said second plate are attached to one another and the humerus with said at least one fastener, and said at least one post extends through the humerus and engages said at least one aperture formed in said prosthesis to connect said prosthesis and said second plate to one another.

2. The system of claim 1, wherein said first surface of said first plate and said second surface of said second plate are adapted to clamp a portion of the humerus therebetween.

3. The system of claim 1, wherein said prosthesis and said first surface of said second plate are adapted to clamp a portion of the humerus therebetween.

4. A system for replacement of at least a portion of a comminuted humeral head, the system comprising:
   a prosthesis having an exterior surface and at least one aperture formed therein, said exterior surface being sized and shaped to approximate the surface of the at least a portion of the comminuted humeral head;
   a first plate including a first surface and an opposite second surface, said first surface adapted to contact an exterior portion of a humerus;
   a second plate including a first surface and an opposite second surface, said first surface including at least one post extending outwardly therefrom, said second surface being adapted to directly contact an interior portion of the humerus, said first surface of said first plate and said second surface of said second plate being adapted to clamp a portion of the humerus therebetween, and said prosthesis and said first surface of said second plate being adapted to clamp a portion of the humerus therebetween; and
   at least one fastener adapted to attach said first and second plates to one another and the humerus, wherein, when the system is position with respect to the humerus, said first plate and said second plate are attached to one another and the humerus with said at least one fastener, and said at least one post extends through the humerus and engages said at least one aperture formed in said prosthesis to connect said prosthesis and said second plate to one another.

5. The system of claim 4, wherein said second plate includes a central longitudinal axis extending through said second plate and said at least one post, said second plate having a first maximum cross-sectional dimension perpendicular to the central longitudinal axis, and said at least one post having a second maximum cross-sectional dimension perpendicular to the central longitudinal axis, the second maximum cross-sectional dimension being less than half of the first maximum cross-sectional dimension.

6. The system of claim 4, wherein said first surface of said second plate is substantially oriented in a first direction and said second surface of said second plate is substantially oriented in a second direction, the first and second directions being opposite to one another.

7. The system of claim 4, wherein said at least one post includes a first end and a second end, said at least one post being attached to the remainder of said second plate at said first end, and said at least one post tapers from said first end toward said second end.

8. The system of claim 7, wherein said second plate includes a central longitudinal axis extending through said second plate and said at least one post, said second plate having a maximum cross-sectional dimension perpendicular to said central longitudinal axis, said first surface of said second plate tapering toward said at least one post from adjacent the first maximum cross-sectional dimension.

9. A system for replacement of at least a portion of a comminuted humeral head, the system comprising:

a prosthesis having an exterior surface and at least one aperture formed therein, said exterior surface being sized and shaped to approximate the surface of the at least a portion of the comminuted humeral head;

a first plate including a first surface and an opposite second surface, said first surface adapted to contact an exterior portion of a humerus;

a second plate including a first surface and an opposite second surface, said first surface of said second plate being substantially oriented in a first direction, said second surface of said second plate being substantially oriented in a second direction, the first and second directions being opposite to one another, said first surface including at least one post extending outwardly therefrom, said second surface being adapted to directly contact an interior portion of the humerus, said second plate including a central longitudinal axis extending through said second plate and said at least one post, said second plate having a first maximum cross-sectional dimension perpendicular to the central longitudinal axis, and said at least one post having a second maximum cross-sectional dimension perpendicular to the central longitudinal axis, the second maximum cross-sectional dimension being less than half of the first maximum cross-sectional dimension; and at least one fastener adapted to attach said first and second plates to one another and the humerus, wherein, when the system is position with respect to the humerus, said first plate and said second plate are attached to one another and the humerus with said at least one fastener, and said at least one post extends through the humerus and engages said at least one aperture formed in said prosthesis to connect said prosthesis and said second plate to one another.

\* \* \* \* \*